(12) United States Patent
Patti et al.

(10) Patent No.: US 7,364,738 B2
(45) Date of Patent: *Apr. 29, 2008

(54) MONOCLONAL ANTIBODIES TO THE CLFA PROTEIN AND METHOD OF USE IN TREATING INFECTIONS

(75) Inventors: Joseph M. Patti, Cumming, GA (US); Jeff T. Hutchins, Cumming, GA (US); Paul Domanski, Atlanta, GA (US); Pratiksha Patel, Duluth, GA (US); Andrea Hall, Acworth, GA (US)

(73) Assignee: Inhibitex, Inc., Alpharetta, GA (US)

( * ) Notice: Subject to any disclaimer, the term of this patent is extended or adjusted under 35 U.S.C. 154(b) by 276 days.

This patent is subject to a terminal disclaimer.

(21) Appl. No.: 11/136,559

(22) Filed: May 25, 2005

(65) Prior Publication Data

US 2005/0287164 A1    Dec. 29, 2005

Related U.S. Application Data

(62) Division of application No. 10/056,052, filed on Jan. 28, 2002, now Pat. No. 6,979,446.

(60) Provisional application No. 60/308,116, filed on Jul. 30, 2001, provisional application No. 60/298,413, filed on Jun. 18, 2001, provisional application No. 60/274,611, filed on Mar. 12, 2001, provisional application No. 60/264,072, filed on Jan. 26, 2001.

(51) Int. Cl.
*A61K 39/00* (2006.01)
*A61K 39/395* (2006.01)
*A61K 39/40* (2006.01)
*C07K 16/00* (2006.01)
*C07K 16/12* (2006.01)

(52) U.S. Cl. ............... 424/165.1; 424/130.1; 424/133.1; 424/150.1; 424/164.1; 530/387.1; 530/387.3; 530/388.1; 530/388.4

(58) Field of Classification Search ............ None
See application file for complete search history.

(56) References Cited

U.S. PATENT DOCUMENTS 6,008,341 A    12/1999  Foster et al.
7,122,320 B2  10/2006  Reiter et al.

FOREIGN PATENT DOCUMENTS

WO    WO-00/12132    3/2000
WO    WO 0064925    11/2000

OTHER PUBLICATIONS

Hall et al., "Characterization of a Protective Monoclonal Antibody Recognizing *Staphylococcus aureus* MSCRAMM Protein Clumping Factor A," Infection and Immunity, vol. 71 No. 12, pp. 6864-6870 (Dec. 2003).*

McDevitt et al, "Identification of the ligand-binding domain of the surface-located fibrinogen receptor (clumping factor) of *Staphylococcus aureus*", 1995, pp. 895-907, vol. 16, No. 5, Molecular Microbiology.

O'Connell et al, "The Fibrinogen-binding MSCRAMM (Clumping Factor) of *Staphylococcus aureus* Has a $Ca^{2+}$-dependent Inhibitory Site", 1998, pp. 6821-6829, vol. 273, No. 12, The Journal of Biological Chemistry.

Hartford et al, "The dipeptide repeat region of the fibrinogen-binding protein (clumping factor) is required for functional expression of the fibrinogen-binding domain on the *Staphylococcus aureus* cell surface", 1997, pp. 1065-1076, Molecular Microbiology.

Hartford et al, "Identification of Residues in the *Staphylococcus aureus* Fibrinogen-binding MSCRAMM Clumping Factor A (ClfA) That Are Important for Ligand Binding", Jan. 26, 2001, pp. 2466-2473, vol. 276, No. 4, The Journal Of Biological Chemistry.

Berg et al, "Granulocytes downregulate T Cell Receptor Zeta Chain by cell contact dependent mechanisms", 2000, pp. 153-154, vol. 73, No. 2-3, Immunology Letters.

Tillman et al, "Both IgM and IgG anti-DNA Antibodies are the product of clonally selective B cell stimulation in (NZB X NZW) F1 mice", 1992, pp. 761-779, vol. 176, Journal of Experimental Medicine.

Klobeck et al, "Subgroup IV of human immunoglobulin K light chains is encoded by a single germline gene", 1985, pg. 6515, vol. 13, No.18, Nucleic Acids Research.

Colque-Navarro et al, "Antibody responses in patients with staphylococcal septicemia against two Staphylococcus aureua fibrinogen binding proteins: Clumping factor and an extracellular fibrinogen binding protein", 2000, pp. 14-20, vol. 7, No. 1, Clinical and Diagnostic Laboratory Immunology.

* cited by examiner

*Primary Examiner*—Zachariah Lucas
(74) *Attorney, Agent, or Firm*—B. Aaron Schulman; Stites & Harbison PLLC

(57) ABSTRACT

Monoclonal antibodies which can bind to the ClfA protein and which are generated from binding subdomains or active fragments of the ClfA protein from *Staphylococcus aureus*, including the active fragments proteins from its fibrinogen binding domain such as Clf40 protein, the Clf33 protein, or ClfA N3, are provided which can be useful in the treatment and protection against infection from staphylococcal bacteria such as *Staphylococcus aureus*. In addition, medical instruments can be treated using the monoclonal antibodies of the invention in order to reduce or eliminate the possibility of their becoming infected or further spreading the infection. In particular, the antibodies of the present invention are advantageous because they can prevent adherence of the bacteria to host cells by impairing or inhibiting the ability of *S. aureus* ClfA to bind to fibrinogen or fibrin, and thus can be utilized in methods or treating or preventing staphylococcal inventions.

1 Claim, 8 Drawing Sheets

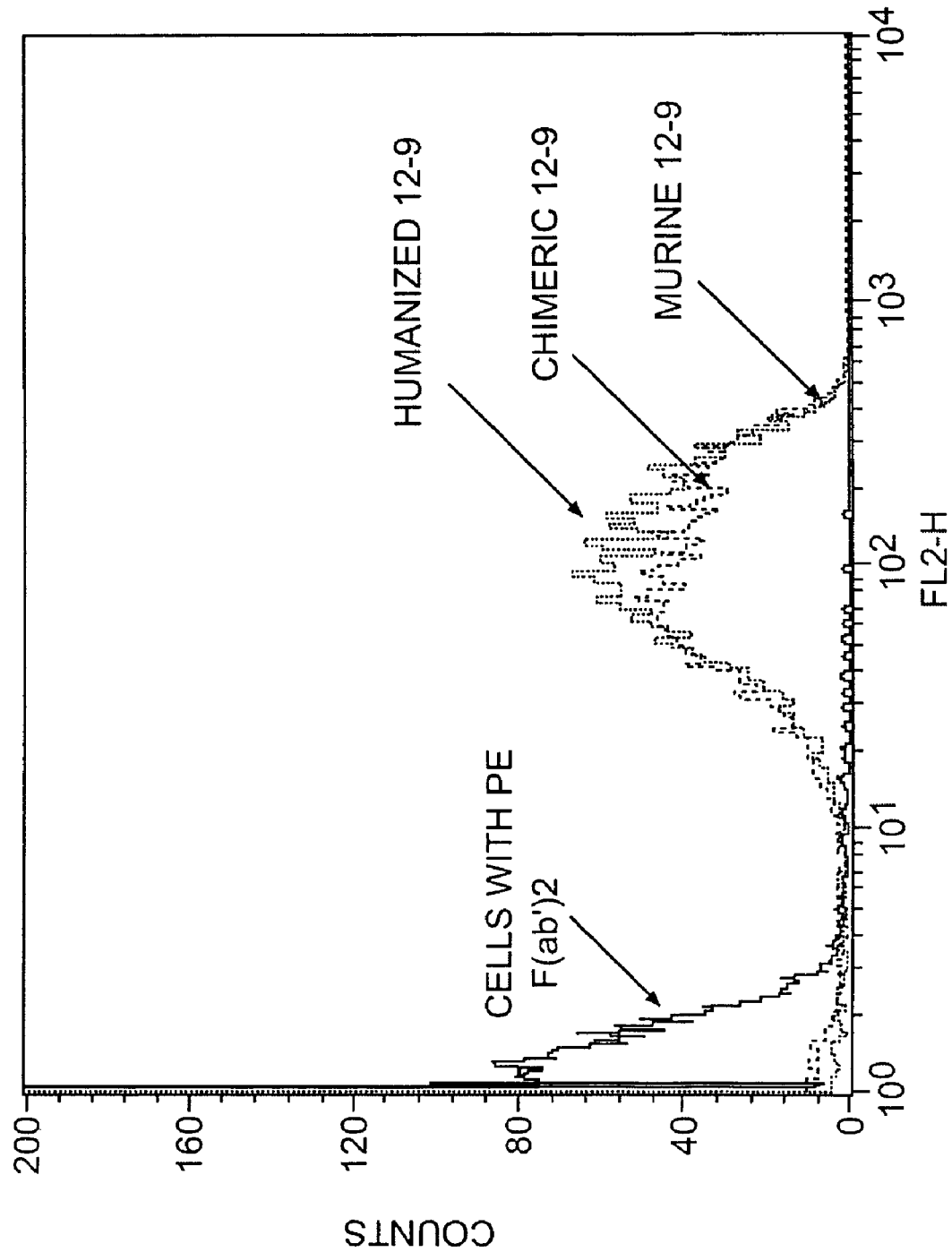

VARIABLE LIGHT CHAIN

| ANTIBODY | CDR 1 | CDR 2 | CDR 3 |
|---|---|---|---|
| 1771 | LSSQSLLDSDGKTFLN | LVSKLDS | WQGTHFPYT |
| 12-9(ClfA) | KSSQSVLYSSNQKNYLA | WASTRES | HQYLSSYT |
| 13-2 | KSSQSVLYSSNQKNYLA | WASTRES | HQYLSSHT |
| 35-006 | KSSQSVLYSSNQKNYLA | WASTRES | HQYLSSYT |
| 35-220 | RSSQSVLYSSNQKNYLA | WASTRES | HQYLSSYT |
| CONSENSUS | KSSQSVLYSSNQKNYLA<br>R | WASTRES | HQYLSSYT<br>H |

VARIABLE HEAVY CHAIN

| ANTIBODY | CDR1 | CDR2 | CDR3 |
|---|---|---|---|
| 1771 | SGFSWH | YIHYSGSTDCNPSLKS | MPDS |
| 12-9(ClfA) | RYSVH | MIWGGGNTDYNSALKS | KGEFYYGYDGFVY |
| 13-2 | RYNIH | MIWGGENTDYNSALKS | AYYGNSWFAY |
| 35-006 | RYSVH | MIWGGGSTDYNSALKS | RLWYFDV |
| 35-220 | RYSVH | MIWGGGNTDYNSALKS | AYYGNSWFAY |
| CONSENSUS | RYSVH<br>NI | MIWGGGNTDYNSALKS<br>ES | AYYGNSWFA***Y<br>KGEFYYGYD<br>RLWYFDV |

FIG. 8

SEQUENCE LISTING

```
<160> NUMBER OF SEQ ID NOS: 29

<210> SEQ ID NO 1
<211> LENGTH: 1560
<212> TYPE: DNA
<213> ORGANISM: Staphylococcus aureus

<400> SEQUENCE: 1
agtgaaaata gtgttacgca atctgatagc gcaagtaacg aaagcaaaag taatgattca     60
agtagcgtta gtgctgcacc taaaacagac gacacaaacg tgagtgatac taaaacatcg    120
tcaaacacta ataatggcga aacgagtgtg gcgcaaaatc cagcacaaca ggaaacgaca    180
caatcatcat caacaaatgc aactacggaa gaaacgccgg taactggtga agctactact    240
acgacaacga atcaagctaa tacaccggca acaactcaat caagcaatac aaatgcggag    300
gaattagtga atcaaacaag taatgaaacg acttttaatg atactaatac agtatcatct    360
gtaaattcac ctcaaaattc tacaaatgcg gaaaatgttt caacaacgca agatacttca    420
actgaagcaa caccttcaaa caatgaatca gctccacaga gtacagatgc aagtaataaa    480
gatgtagtta atcaagcggt taatacaagt gcgcctagaa tgagagcatt tagtttagcg    540
```

-continued

```
gcagtagctg cagatgcacc ggcagctggc acagatatta cgaatcagtt gacgaatgtg    600
acagttggta ttgactctgg tacgactgtg tatccgcacc aagcaggtta tgtcaaactg    660
aattatggtt tttcagtgcc taattctgct gttaaaggtg acacattcaa ataactgta    720
cctaaagaat taaacttaaa tggtgtaact tcaactgcta aagtgccacc aattatggct    780
ggagatcaag tattggcaaa tggtgtaatc gatagtgatg gtaatgttat ttatacattt    840
acagactatg taaatactaa agatgatgta aaagcaactt tgaccatgcc cgcttatatt    900
gaccctgaaa atgttaaaaa gacaggtaat gtgacattgg ctactggcat aggtagtaca    960
acagcaaaca aaacagtatt agtagattat gaaaaatatg gtaagtttta aacttatct    1020
attaaaggta caattgacca atcgataaa acaaataata cgtatcgtca gacaatttat    1080
gtcaatccaa gtggagataa cgttattgcg ccggttttaa caggtaattt aaaaccaaat    1140
acggatagta atgcattaat agatcagcaa aatacaagta ttaaagtata taagtagat    1200
aatgcagctg atttatctga agttactttt gtgaatccag aaaactttga ggatgtcact    1260
aatagtgtga atattacatt cccaaatcca atcaatata agtagagtt taatacgcct    1320
gatgatcaaa ttacaacacc gtatatagta gttgttaatg gtcatattga tccgaatagc    1380
aaaggtgatt tagctttacg ttcaacttta tatgggtata actcgaatat aatttggcgc    1440
tctatgtcat gggacaacga agtagcattt aataacggat caggttctgg tgacggtatc    1500
gataaaccag ttgttcctga caacctgat gagcctggtg aaattgaacc aattccagag    1560
```

<210> SEQ ID NO 2
<211> LENGTH: 520
<212> TYPE: PRT
<213> ORGANISM: Staphylococcus aureus

<400> SEQUENCE: 2

```
Ser Glu Asn Ser Val Thr Gln Ser Asp Ser Ala Ser Asn Glu Ser Lys
1               5                   10                  15

Ser Asn Asp Ser Ser Val Ser Ala Ala Pro Lys Thr Asp Asp Thr
            20                  25                  30

Asn Val Ser Asp Thr Lys Thr Ser Ser Asn Thr Asn Asn Gly Glu Thr
        35                  40                  45

Ser Val Ala Gln Asn Pro Ala Gln Gln Glu Thr Thr Gln Ser Ser Ser
    50                  55                  60

Thr Asn Ala Thr Thr Glu Glu Thr Pro Val Thr Gly Glu Ala Thr Thr
65                  70                  75                  80

Thr Thr Thr Asn Gln Ala Asn Thr Pro Ala Thr Thr Gln Ser Ser Asn
                85                  90                  95

Thr Asn Ala Glu Glu Leu Val Asn Gln Thr Ser Asn Glu Thr Thr Phe
            100                 105                 110

Asn Asp Thr Asn Thr Val Ser Ser Val Asn Ser Pro Gln Asn Ser Thr
        115                 120                 125

Asn Ala Glu Asn Val Ser Thr Thr Gln Asp Thr Ser Thr Glu Ala Thr
    130                 135                 140

Pro Ser Asn Asn Glu Ser Ala Pro Gln Ser Thr Asp Ala Ser Asn Lys
145                 150                 155                 160

Asp Val Val Asn Gln Ala Val Asn Thr Ser Ala Pro Arg Met Arg Ala
                165                 170                 175

Phe Ser Leu Ala Ala Val Ala Ala Asp Ala Pro Ala Ala Gly Thr Asp
            180                 185                 190

Ile Thr Asn Gln Leu Thr Asn Val Thr Val Gly Ile Asp Ser Gly Thr
```

-continued

```
                195                 200                 205
    Thr Val Tyr Pro His Gln Ala Gly Tyr Val Lys Leu Asn Tyr Gly Phe
        210                 215                 220
    Ser Val Pro Asn Ser Ala Val Lys Gly Asp Thr Phe Lys Ile Thr Val
    225                 230                 235                 240
    Pro Lys Glu Leu Asn Leu Asn Gly Val Thr Ser Thr Ala Lys Val Pro
                    245                 250                 255
    Pro Ile Met Ala Gly Asp Gln Val Leu Ala Asn Gly Val Ile Asp Ser
                260                 265                 270
    Asp Gly Asn Val Ile Tyr Thr Phe Thr Asp Tyr Val Asn Thr Lys Asp
            275                 280                 285
    Asp Val Lys Ala Thr Leu Thr Met Pro Ala Tyr Ile Asp Pro Glu Asn
        290                 295                 300
    Val Lys Lys Thr Gly Asn Val Thr Leu Ala Thr Gly Ile Gly Ser Thr
    305                 310                 315                 320
    Thr Ala Asn Lys Thr Val Leu Val Asp Tyr Glu Lys Tyr Gly Lys Phe
                    325                 330                 335
    Tyr Asn Leu Ser Ile Lys Gly Thr Ile Asp Gln Ile Asp Lys Thr Asn
                340                 345                 350
    Asn Thr Tyr Arg Gln Thr Ile Tyr Val Asn Pro Ser Gly Asp Asn Val
            355                 360                 365
    Ile Ala Pro Val Leu Thr Gly Asn Leu Lys Pro Asn Thr Asp Ser Asn
        370                 375                 380
    Ala Leu Ile Asp Gln Gln Asn Thr Ser Ile Lys Val Tyr Lys Val Asp
    385                 390                 395                 400
    Asn Ala Ala Asp Leu Ser Glu Ser Tyr Phe Val Asn Pro Glu Asn Phe
                    405                 410                 415
    Glu Asp Val Thr Asn Ser Val Asn Ile Thr Phe Pro Asn Pro Asn Gln
                420                 425                 430
    Tyr Lys Val Glu Phe Asn Thr Pro Asp Asp Gln Ile Thr Thr Pro Tyr
            435                 440                 445
    Ile Val Val Val Asn Gly His Ile Asp Pro Asn Ser Lys Gly Asp Leu
        450                 455                 460
    Ala Leu Arg Ser Thr Leu Tyr Gly Tyr Asn Ser Asn Ile Ile Trp Arg
    465                 470                 475                 480
    Ser Met Ser Trp Asp Asn Glu Val Ala Phe Asn Asn Gly Ser Gly Ser
                    485                 490                 495
    Gly Asp Gly Ile Asp Lys Pro Val Pro Glu Gln Pro Asp Glu Pro
                500                 505                 510
    Gly Glu Ile Glu Pro Ile Pro Glu
            515                 520

<210> SEQ ID NO 3
<211> LENGTH: 990
<212> TYPE: DNA
<213> ORGANISM: Staphylococcus aureus

<400> SEQUENCE: 3
gtagctgcag atgcaccggc agctggcaca gatattacga atcagttgac gaatgtgaca      60
gttggtattg actctggtac gactgtgtat ccgcaccaag caggttatgt caaactgaat     120
tatggttttt cagtgcctaa ttctgctgtt aaaggtgaca cattcaaaat aactgtacct     180
aaagaattaa acttaaatgg tgtaacttca actgctaaag tgccaccaat tatggctgga     240
gatcaagtat tggcaaatgg tgtaatcgat agtgatggta atgttattta tacatttaca     300
```

```
gactatgtaa atactaaaga tgatgtaaaa gcaactttga ccatgcccgc ttatattgac    360
cctgaaaatg ttaaaagac aggtaatgtg acattggcta ctggcatagg tagtacaaca    420
gcaaacaaaa cagtattagt agattatgaa aaatatggta agttttataa cttatctatt    480
aaaggtacaa ttgaccaaat cgataaaaca ataatacgt atcgtcagac aatttatgtc    540
aatccaagtg gagataacgt tattgcgccg gttttaacag gtaatttaaa accaaatacg    600
gatagtaatg cattaataga tcagcaaaat acaagtatta agtatataa agtagataat    660 gcagctgatt tatctgaaag ttactttgtg aatccagaaa actttgagga tgtcactaat    720
agtgtgaata ttcattccc aaatccaaat caatataaag tagagtttaa tacgcctgat    780
gatcaaatta caacaccgta tagtagtt gttaatggtc atattgatcc gaatagcaaa    840
ggtgatttag ctttacgttc aactttatat gggtataact cgaatataat ttggcgctct    900
atgtcatggg acaacgaagt agcatttaat aacggatcag gttctggtga cggtatcgat    960
aaaccagttg ttcctgaaca acctgatgag                                    990
```

<210> SEQ ID NO 4
<211> LENGTH: 331
<212> TYPE: PRT
<213> ORGANISM: Staphylococcus aureus

<400> SEQUENCE: 4

```
Met Val Ala Ala Asp Ala Pro Ala Ala Gly Thr Asp Ile Thr Asn Gln
1               5                   10                  15

Leu Thr Asn Val Thr Val Gly Ile Asp Ser Gly Thr Thr Val Tyr Pro
                20                  25                  30

His Gln Ala Gly Tyr Val Lys Leu Asn Tyr Gly Phe Ser Val Pro Asn
            35                  40                  45

Ser Ala Val Lys Gly Asp Thr Phe Lys Ile Thr Val Pro Lys Glu Leu
        50                  55                  60

Asn Leu Asn Gly Val Thr Ser Thr Ala Lys Val Pro Pro Ile Met Ala
65                  70                  75                  80

Gly Asp Gln Val Leu Ala Asn Gly Val Ile Ser Asp Gly Asn Val
                85                  90                  95

Ile Tyr Thr Phe Thr Asp Tyr Val Asn Thr Lys Asp Asp Val Lys Ala
            100                 105                 110

Thr Leu Thr Met Pro Ala Tyr Ile Asp Pro Glu Asn Val Lys Lys Thr
        115                 120                 125

Gly Asn Val Thr Leu Ala Thr Gly Ile Gly Ser Thr Thr Ala Asn Lys
    130                 135                 140

Thr Val Leu Val Asp Tyr Glu Lys Tyr Gly Lys Phe Tyr Asn Leu Ser
145                 150                 155                 160

Ile Lys Gly Thr Ile Asp Gln Ile Asp Lys Thr Asn Thr Tyr Arg
            165                 170                 175

Gln Thr Ile Tyr Val Asn Pro Ser Gly Asp Asn Val Ile Ala Pro Val
        180                 185                 190

Leu Thr Gly Asn Leu Lys Pro Asn Thr Asp Ser Asn Ala Leu Ile Asp
    195                 200                 205

Gln Gln Asn Thr Ser Ile Lys Val Tyr Lys Val Asp Asn Ala Ala Asp
    210                 215                 220

Leu Ser Glu Ser Tyr Phe Val Asn Pro Glu Asn Phe Glu Asp Val Thr
225                 230                 235                 240

Asn Ser Val Asn Ile Thr Phe Pro Asn Pro Asn Gln Tyr Lys Val Glu
```

```
                    245                 250                 255
Phe Asn Thr Pro Asp Asp Gln Ile Thr Thr Pro Tyr Ile Val Val
                260                 265                 270

Asn Gly His Ile Asp Pro Asn Ser Lys Gly Asp Leu Ala Leu Arg Ser
            275                 280                 285

Thr Leu Tyr Gly Tyr Asn Ser Asn Ile Ile Trp Arg Ser Met Ser Trp
        290                 295                 300

Asp Asn Glu Val Ala Phe Asn Asn Gly Ser Ser Gly Asp Gly Ile
305                 310                 315                 320

Asp Lys Pro Val Val Pro Glu Gln Pro Asp Glu
                325                 330

<210> SEQ ID NO 5
<211> LENGTH: 336
<212> TYPE: DNA
<213> ORGANISM: Staphylococcus aureus

<400> SEQUENCE: 5
aacattatga tgacacagtc gccatcatct ctggctgtgt ctgcaggaga aaaggtcact      60
atgagctgta agtccagtca agtgtttta tacagttcaa atcagaagaa ctacttggcc     120
tggtaccagc agaaaccagg gcagtctcct aaactactga tctactgggc atccactagg     180
gaatctggtg tccctgatcg cttcacaggc agtggatctg gacagattt tactcttacc     240 atcaacagtg tacaagctga agacctggca gtttattact gtcatcaata cctctcctcg     300
cacacgttcg agggggggac caagctggaa ataaaa                                336

<210> SEQ ID NO 6
<211> LENGTH: 112
<212> TYPE: PRT
<213> ORGANISM: Staphylococcus aureus

<400> SEQUENCE: 6

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ala Glu Asp Leu Ala Val Tyr Tyr Cys His Gln
                85                  90                  95

Tyr Leu Ser Ser His Thr Phe Gly Gly Gly Thr Lys Leu Glu Ile Lys
            100                 105                 110

<210> SEQ ID NO 7
<211> LENGTH: 354
<212> TYPE: DNA
<213> ORGANISM: Staphylococcus aureus

<400> SEQUENCE: 7
caggtgcatc tgaaggagtc aggacctggc ctggtggcac cctcacagag cctgtccatc      60
acatgcactg tctctggatt ctcattatcc agatataata tacactgggt tcgccagcct     120
ccaggaaagg gtctggagtg gctgggaatg atatggggtg gtgaaaacac agactataat     180
```
tcagctctca aatccagact gagcatcagc aaggacaact ccaagagcca agtttctta    240 aaaatgaaca gtctgcaaac tgatgacaca gccatgtact actgtgccag cgcctactat    300
ggtaactcct ggtttgctta ctggggccag gggactctgg tcactgtctc tgca          354

<210> SEQ ID NO 8
<211> LENGTH: 118
<212> TYPE: PRT
<213> ORGANISM: Staphylococcus aureus

<400> SEQUENCE: 8

Gln Val His Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Asn Ile His Trp Val Arg Gln Pro Pro Gly Lys Gly Leu Glu Trp Leu
        35                  40                  45

Gly Met Ile Trp Gly Gly Glu Asn Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Ser Ala Tyr Tyr Gly Asn Ser Trp Phe Ala Tyr Trp Gly Gln Gly Thr
            100                 105                 110

Leu Val Thr Val Ser Ala
        115

<210> SEQ ID NO 9
<211> LENGTH: 336
<212> TYPE: DNA
<213> ORGANISM: Staphylococcus aureus

<400> SEQUENCE: 9
aacattatga tgacacagtc gccatcatct ctggctgtgt ctgcaggaga aaaggtcact    60
atgagctgta agtccagtca agtgttttta tacagttcaa atcagaagaa ctacttggcc    120
tggtaccagc agaaaccagg cagtctcct aaactgctga tctactgggc atccactagg    180
gaatctggtg tccctgatcg cttcacaggc agtggatctg gacagattt tactcttacc    240 atcagcagtg tacaagctga agacctggca gtttattact gtcatcaata cctctcctcg    300
tacacgttcg gaggggggac caagctggaa ataaaa                              336

<210> SEQ ID NO 10
<211> LENGTH: 112
<212> TYPE: PRT
<213> ORGANISM: Staphylococcus aureus

<400> SEQUENCE: 10

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

```
Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys His Gln
                 85                  90                  95

Tyr Leu Ser Ser Tyr Thr Phe Gly Gly Gly Thr Lys Leu Glu Ile Lys
            100                 105                 110

<210> SEQ ID NO 11
<211> LENGTH: 363
<212> TYPE: DNA
<213> ORGANISM: Staphylococcus aureus

<400> SEQUENCE: 11
caggtgcagc tgaaggagtc aggacctggc ctggtggcac cctcacagag cctgtccatc      60
acatgcgcta tctctgggtt ctcattatcc agatatagtg tacactgggt tcgccagcct     120
ccaggaaagg gtctggagtg gctgggaatg atatggggtg gtggaaacac agactataat     180
tcagctctca aatccagact gagcatcagc aaggacaact ccaagagcca gttttcttta     240
aaaatgaaca gtctgcaaac tgatgacaca gccatgtatt actgtgccag aaaaggggaa     300
ttctactatg gttacgacgg gtttgtttac tggggccaag ggactctggt cactgtctct     360
gca                                                                  363

<210> SEQ ID NO 12
<211> LENGTH: 121
<212> TYPE: PRT
<213> ORGANISM: Staphylococcus aureus

<400> SEQUENCE: 12

Gln Val Gln Leu Lys Glu Ser Gly Pro Gly Leu Val Ala Pro Ser Gln
  1               5                  10                  15

Ser Leu Ser Ile Thr Cys Ala Ile Ser Gly Phe Ser Leu Ser Arg Tyr
                 20                  25                  30

Ser Val His Trp Val Arg Gln Pro Pro Gly Lys Gly Leu Glu Trp Leu
             35                  40                  45

Gly Met Ile Trp Gly Gly Gly Asn Thr Asp Tyr Asn Ser Ala Leu Lys
         50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
                 85                  90                  95

Arg Lys Gly Glu Phe Tyr Tyr Gly Tyr Asp Gly Phe Val Tyr Trp Gly
            100                 105                 110

Gln Gly Thr Leu Val Thr Val Ser Ala
        115                 120

<210> SEQ ID NO 13
<211> LENGTH: 336
<212> TYPE: DNA
<213> ORGANISM: Staphylococcus aureus

<400> SEQUENCE: 13
aacattatga tgacacagtc gccatcatct ctggctgtgt ctgcaggaga aaaggtcact      60
atgagctgta ggtccagtca agtgttttta tacagttcaa atcagaagaa ctacttggcc     120
tggtaccagc agaaaccagg gcagtctcct acactgctga tctactgggc atccactagg     180
gaatctggtg tccctgatcg cttcacaggc agtggatctg gacagatttt tactcttacc     240
```

```
atcagcagtg tacaagctga agacctggca gtttattact gtcatcaata cctctcctcg    300
tacacgttcg gagggggac caagctggaa ataaaa                               336
```

<210> SEQ ID NO 14
<211> LENGTH: 112
<212> TYPE: PRT
<213> ORGANISM: Staphylococcus aureus

<400> SEQUENCE: 14

```
Asn Ile Met Met Thr Gln Ser Pro Ser Ser Leu Ala Val Ser Ala Gly
1               5                   10                  15

Glu Lys Val Thr Met Ser Cys Arg Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Thr Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
            100                 105                 110
```

<210> SEQ ID NO 15
<211> LENGTH: 354
<212> TYPE: DNA
<213> ORGANISM: Staphylococcus aureus

<400> SEQUENCE: 15

```
caggtgcagc tgaaggagtc aggacctggc ctggtggcac cctcacagag cctgtccatc    60
acatgcactg tctctgggtt ctcattatcc agatatagtg tacactgggt tcgccagcct    120
ccaggaaagg gtctggagtg gctgggaatg atatggggtg gtggaaacac agactataat    180
tcagctctca aatccagact gagcatcacc aaggacaact ccaagagcca agttttctta    240
aaaatgaaca gtctgcaaac tgatgacaca gccatgtact actgtgccac cgcctactat    300
ggtaactcct ggtttgctta ctggggccaa gggactctgg tcactgtctc tgca          354
```

<210> SEQ ID NO 16
<211> LENGTH: 118
<212> TYPE: PRT
<213> ORGANISM: Staphylococcus aureus

<400> SEQUENCE: 16

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Asn Thr Asp Tyr Asn Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95
```

```
            Thr Ala Tyr Tyr Gly Asn Ser Trp Phe Ala Tyr Trp Gly Gln Gly Thr
                        100                 105                 110

Leu Val Thr Val Ser Ala
                    115

<210> SEQ ID NO 17
<211> LENGTH: 336
<212> TYPE: DNA
<213> ORGANISM: Staphylococcus aureus

<400> SEQUENCE: 17
gacattgtga tgacacagtc gccagactct ctggctgtgt ctctgggaga aagggtcact      60
atgaactgta agtccagtca aagtgtttta tacagttcaa atcagaagaa ctacttggcc     120
tggtaccagc agaaaccagg gcagtctcct aaactgctga tctactgggc atccactagg     180
gaatctggtg tccctgatcg cttcagcggc agtggatctg gacagattt tactcttacc      240 atcagcagtg tacaagctga agacctggca gtttattact gtcatcaata cctctcctcg     300
tacacgttcg gaggggggac caagctggaa ataaaa                               336

<210> SEQ ID NO 18
<211> LENGTH: 112
<212> TYPE: PRT
<213> ORGANISM: Staphylococcus aureus

<400> SEQUENCE: 18

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Val Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
            100                 105                 110

<210> SEQ ID NO 19
<211> LENGTH: 363
<212> TYPE: DNA
<213> ORGANISM: Staphylococcus aureus

<400> SEQUENCE: 19
caggtgcagc tgaaggagtc aggacctggc ctggtgaagc cctcacagac cctgtccatc      60
acatgcacca tctctgggtt ctcattatcc agatatagtg tacactgggt tcgccagcct     120
ccaggaaagg gtctggagtg gctgggaatg atatggggtg gtggaaacac agactataat     180
tcagctctca atccagact gagcatcagc aaagacaact ccaagaacca gttttctta      240 aaaatgaaca gtctgaccgc cgctgacaca gccgtgtatt actgtgccag aaaaggggaa     300
ttctactatg gttacgacgg gtttgtttac tggggccaag ggactctggt cactgtctct     360
tcc                                                                   363

<210> SEQ ID NO 20
```

<211> LENGTH: 121
<212> TYPE: PRT
<213> ORGANISM: Staphylococcus aureus

<400> SEQUENCE: 20

Gln Val Gln Leu Lys Glu Ser Gly Pro Gly Leu Val Lys Pro Ser Gln
1               5                   10                  15

Thr Leu Ser Ile Thr Cys Thr Ile Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Asn Thr Asp Tyr Asn Ser Ala Leu Lys
    50                  55                  60

Ser Arg Leu Ser Ile Ser Lys Asp Asn Ser Lys Asn Gln Val Phe Leu
65                  70                  75                  80

Lys Met Asn Ser Leu Thr Ala Ala Asp Thr Ala Val Tyr Tyr Cys Ala
                85                  90                  95

Arg Lys Gly Glu Phe Tyr Tyr Gly Tyr Asp Gly Phe Val Tyr Trp Gly
            100                 105                 110

Gln Gly Thr Leu Val Thr Val Ser Ser
        115                 120

<210> SEQ ID NO 21
<211> LENGTH: 336
<212> TYPE: DNA
<213> ORGANISM: Staphylococcus aureus

<400> SEQUENCE: 21
aacattatga tgacacagtc gccatcatct ctggctgtgt ctgcaggaga aaaggtcact      60
atgagctgta agtccagtca aagtgtttta tacagttcaa atcagaagaa ctacttggcc    120
tggtaccagc agaaaccagg gcagtctcct aaactgctga tctactgggc atccactagg    180
gaatctggtg tccctgatcg cttcacaggc agtggatctg ggacagattt tactcttacc    240
atcagcagtg tacaagctga agacctggca gtttattgct gtcatcaata cctctcctcg    300
tacacgttcg gagggggac cgagctggaa ataaaa                               336

<210> SEQ ID NO 22
<211> LENGTH: 112
<212> TYPE: PRT
<213> ORGANISM: Staphylococcus aureus

<400> SEQUENCE: 22

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Cys Cys His Gln
                85                  90                  95

Tyr Leu Ser Ser Tyr Thr Phe Gly Gly Gly Thr Glu Leu Glu Ile Lys
            100                 105                 110

```
<210> SEQ ID NO 23
<211> LENGTH: 345
<212> TYPE: DNA
<213> ORGANISM: Staphylococcus aureus

<400> SEQUENCE: 23
caggtgcagc tgaaggagtc aggacctggc ctggtggcac cctcacagag cctgtccatc      60
acatgcactg tctctgggtt ctcattatcc agatatagtg tacactgggt tcgccagcct     120
ccaggaaagg gtctggagtg gctgggaatg atatggggtg gtggaagcac agactataat     180
tcagctctca aatccagact gaacatcagc aaggacaact ccaagagcca agttttctta     240
aaaatgaaca gtctgcaaac tgatgacaca gccatgtact actgtgccag aaggctctgg     300
tacttcgatg tctggggcgc agggaccacg gtcaccgtct cctca                    345

<210> SEQ ID NO 24
<211> LENGTH: 115
<212> TYPE: PRT
<213> ORGANISM: Staphylococcus aureus

<400> SEQUENCE: 24

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Asn Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Arg Leu Trp Tyr Phe Asp Val Trp Gly Ala Gly Thr Thr Val Thr
            100                 105                 110

Val Ser Ser
        115

<210> SEQ ID NO 25
<211> LENGTH: 5
<212> TYPE: PRT
<213> ORGANISM: Staphylococcus aureus

<400> SEQUENCE: 25

Arg Tyr Ser Val His
1               5

<210> SEQ ID NO 26
<211> LENGTH: 16
<212> TYPE: PRT
<213> ORGANISM: Staphylococcus aureus

<400> SEQUENCE: 26

Met Ile Trp Gly Gly Gly Asn Thr Asp Tyr Asn Ser Ala Leu Lys Ser
1               5                   10                  15

<210> SEQ ID NO 27
<211> LENGTH: 17
<212> TYPE: PRT
<213> ORGANISM: Staphylococcus aureus
```

```
<400> SEQUENCE: 27

Lys Ser Ser Gln Ser Val Leu Tyr Ser Ser Asn Gln Lys Asn Tyr Leu
1               5                   10                  15
Ala

<210> SEQ ID NO 28
<211> LENGTH: 7
<212> TYPE: PRT
<213> ORGANISM: Staphylococcus aureus

<400> SEQUENCE: 28

Trp Ala Ser Thr Arg Glu Ser
1               5

<210> SEQ ID NO 29
<211> LENGTH: 8
<212> TYPE: PRT
<213> ORGANISM: Staphylococcus aureus

<400> SEQUENCE: 29

His Gln Tyr Leu Ser Ser Tyr Thr
1               5
```

MONOCLONAL ANTIBODIES TO THE CLFA PROTEIN AND METHOD OF USE IN TREATING INFECTIONS

CROSS REFERENCE TO RELATED APPLICATIONS

The present application is a divisional patent application of U.S. patent application Ser. No. 10/056,052, filed Jan. 28, 2002, now U.S. Pat. No. 6,979,446, which claims the benefit of U.S. provisional applications Ser. No. 60/308,116, filed Jul. 30, 2001, Ser. No. 60/298,413, filed Jun. 18, 2001, Ser. No. 60/274,611, filed Mar. 12, 2001, and Ser. No. 60/264,072, filed Jan. 26, 2001.

FIELD OF THE INVENTION

The present invention relates in general to antibodies that have been generated against clumping factor A (or ClfA), a surface localized protein expressed in *Staphylococcus aureus* and other *staphylococcus* bacteria, and in particular to monoclonal antibodies against the ClfA protein and its active fragments or proteins from its fibrinogen binding domain such as Clf40, Clf33, or ClfA N3, and their use in inhibiting the binding of the ClfA protein to fibrinogen or fibrin and treating or preventing *S. aureus* infections.

BACKGROUND OF THE INVENTION

The successful colonization of the host is a process required for most microorganisms to cause infections in animals and humans. Microbial adhesion is the first crucial step in a series of events that can eventually lead to disease. Pathogenic microorganisms colonize the host by attaching to host tissues or serum conditioned implanted biomaterials, such as catheters, artificial joints, and vascular grafts, through specific adhesins present on the surface of the bacteria. MSCRAMM™s (Microbial Surface Components Recognizing Adhesive Matrix Molecules) are a family of cell surface adhesins that recognize and specifically bind to distinct components in the host's extracellular matrix. Once the bacteria have successfully adhered and colonized host tissues, their physiology is dramatically altered and damaging components such as toxins and proteolytic enzymes are secreted. Moreover, adherent bacteria often produce a biofilm and quickly become more resistant to the killing effect of most antibiotics.

*S. aureus* causes a spectrum of infections that range from cutaneous lesions such as wound infections, impetigo, and furuncles to life-threatening conditions that include pneumonia, septic arthritis, sepsis, endocarditis, and biomaterial related infections. *S. aureus* is known to express a repertoire of different MSCRAMMs that can act individually or in concert to facilitate microbial adhesion to specific host tissue components. MSCRAMMs provide an excellent target for immunological attack by antibodies, in particular monoclonal antibodies. The presence of the appropriate anti-MSCRAMM high affinity antibodies can have a double-edged attack, first the antibodies can prevent microbial adherence and second the increased levels of MSCRAMM antibodies facilitate a rapid clearance of the organism from the body through opsonophagocytic killing.

However, it has still remained a problem to identify and utilize the information concerning MSCRAMM™s from *S. aureus* such as the ClfA protein to generate effective monoclonal antibodies because of the variability in the binding properties of the different MSCRAMM™s and their role in infectivity and spread of bacterial infections. In particular, it has been a problem to develop monoclonal antibodies which can bind to ClfA and which can be use to inhibit or impair the binding of staphylococcal ClfA to fibrinogen or fibrin and thus be useful in methods of preventing or treating staphylococcal infections. It has thus remained a highly desirable goal in the field of infectious diseases to develop monoclonal antibodies and other compositions which are successful in treating and preventing a wide variety of staph infections, particularly by inhibiting or impairing the bacteria's ability to bind to fibrinogen or fibrin.

SUMMARY OF THE INVENTION

Accordingly, it is an object of the present invention to provide monoclonal antibodies that can bind to the *S. aureus* ClfA protein and thus be useful in methods to treat or prevent staphylococcal infections.

It is also an object of the present invention to provide monoclonal antibodies which are able to bind ClfA, and which are generated from the binding subdomains of the *S. aureus* ClfA protein, including the Clf40, Clf33 and ClfA N3 proteins, or active portions thereof, to be utilized in methods of treating or protecting against staphylococcal infections.

It is also an object of the present invention to provide a monoclonal antibodies to the Clf40, Clf33 and ClfA N3 proteins which can be useful in preventing adherence of Staphylococcal bacteria by inhibiting or impairing the binding of the ClfA protein to fibrinogen or fibrin.

It is a further object of the present invention to provide antibodies and antisera which can recognize the fibrinogen binding A domain of the ClfA protein and which can thus be useful in methods of treating, preventing, identifying or diagnosing staphylococcal infections.

It is a further object of the invention to provide amino acid sequences and the nucleic acid sequences which code for the variable light sequence and the variable heavy sequences of the monoclonal antibodies of the present invention.

It is still further an object of the present invention to provide a monoclonal antibody to ClfA which is protective against infection from *S. aureus*, and which can achieve cross-reactivity against other types of staph infection.

These and other objects are provided by virtue of the present invention which comprises the isolation and use of monoclonal antibodies to the ClfA protein and/or its binding subdomains, including the proteins Clf40, Clf33, and ClfA N3, for the prevention and treatment of *Staphylococcus* infections. The present application thus describes the discovery, production, characterization, and in vivo evaluation of monoclonal antibodies against ClfA, a surface localized protein expressed by virtually every *S. aureus* strain. Data presented here clearly demonstrate that monoclonal antibodies against ClfA and its active subdomains such as Clf40, Clf33 and N3 can be used to treat or protect against *S. aureus* infections.

The discovery and isolation of anti-ClfA monoclonal antibodies in accordance with the present invention can thus be used to impair or inhibit binding of the ClfA protein to fibrinogen or fibrin and thus be useful in methods or treating or preventing staph infections. In accordance with the invention, suitable compositions and vaccines based on the isolated ClfA protein subdomains and antibodies raised thereto, as well as methods for their use, are also contemplated.

These embodiments and other alternatives and modifications within the spirit and scope of the disclosed invention will become readily apparent to those skilled in the art from

BRIEF DESCRIPTION OF THE DRAWING FIGURES

FIG. 7 is a graph showing the comparative binding of *S. aureus* using the 12-9 murine, 12-9 chimeric, and 12-9 humanized monoclonal antibodies in accordance with the present invention.

Figure 1:
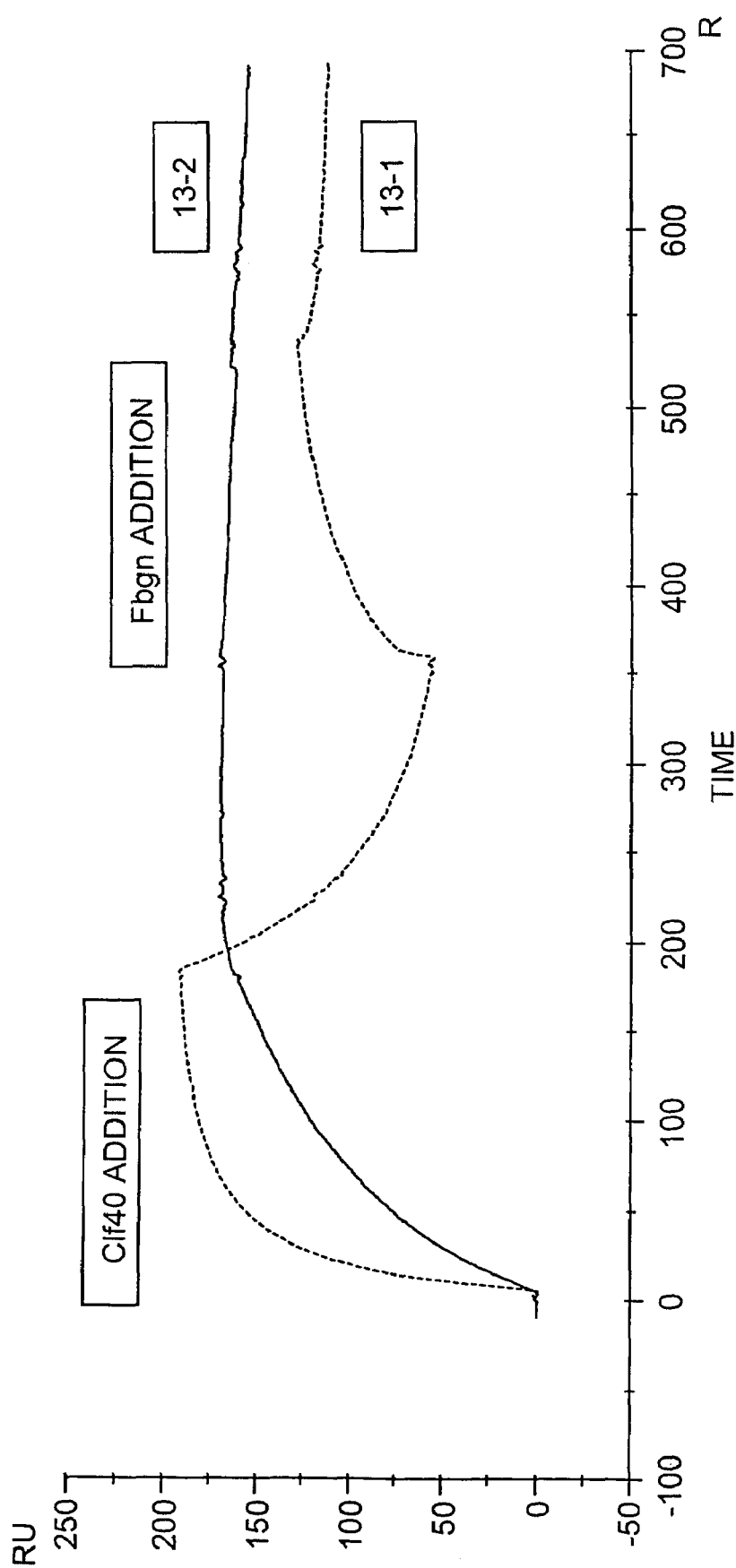
FIG. 1 is a graph of a biacore analysis used to measure ClfA binding and subsequent binding/inhibition of fibrinogen when monoclonal antibodies 13-1 or 13-2 in accordance with the present invention are bound to a chip using rabbit anti-mouse Fc (RAM-Fc) antibody.

FIG. 8 is a depiction of the variable heavy chain and variable light sequences of the monoclonal antibodies of the present invention showing the conserved sequences in the CDR1, CDR2 and CDR3 regions, including SEQ ID NOS 25-445. In particular, these sequences include variable light chain CDR's 1-3, respectively for the antibodies as follows: Antibody 1771: SEQ ID NOS. 30, 31 and 32; Antibody 12-9: SEQ ID NOS. 27, 28 and 29; Antibody 13-2: SEQ ID NOS. 27, 28 and 45; Antibody 35-006: SEQ ID NOS. 27, 28 and 29; Antibody 35-220: SEQ ID NOS. 33, 28 and 29; and Consensus: SEQ ID NOS. 27, 28 and 29. In addition, these sequences include variable heavy chain CDR's 1-3, respectively for the antibodies as follows: Antibody 1771: SEQ ID NOS. 34, 35 and 36; Antibody 12-9: SEQ ID NOS. 25, 26 and 37; Antibody 13-2: SEQ ID NOS. 38, 40 and 42; Antibody 35-006: SEQ ID NOS. 25, 41 and 42; and Antibody 35-220: SEQ ID NOS. 25, 26 and 42. The Consensus sequence has a CDR1 region of SEQ ID NO: 25, a CDR2 region of SEQ ID NO: 26; and a CDR3 region of SEQ ID NO: 43, SEQ ID NO: 44, or SEQ ID NO: 42.

DETAILED DESCRIPTION OF THE PREFERRED EMBODIMENTS

In accordance with the present invention, there are provided monoclonal antibodies which can bind to the ClfA protein of *S. aureus*, and these monoclonal antibodies have been raised against active binding subdomain proteins including Clf40, Clf33, and the ClfA N3 regions which have been isolated and purified by the present inventors. The monoclonal antibodies in accordance with the invention have been shown to treat or protect against *S. aureus* infections.

Previously, McDevitt et al (McDevitt et al, 1994, Mol. Microbiol. 11, 237-248) identified a 92 kDa surface protein, from *S. aureus* strain Newman, demonstrated to be responsible for the fibrinogen-dependent clumping of bacteria, and this is now disclosed in U.S. Pat. No. 6,177,084, incorporated herein by reference. The gene, designated ClfA, was cloned and sequenced, and this is disclosed in U.S. Pat. No. 6,008,341, also incorporated by reference, and this region, representing a 896 amino acid protein as predicted from the DNA sequence, mediates adherence of bacteria to fibrinogen-coated surfaces, thereby identifying ClfA as a MSCRAMM™. The ClfA gene consists of a cytoplasmic domain, a transmembrane domain, an anchoring domain to the cell wall and a region (designated R) that connects the cell anchoring domains with the $NH_2$-terminal region A (composed of a unique 520 residue segment). The fibrinogen-binding domain of this MSCRAMM has been localized to a 218-residue segment within region A. McDevitt et al (McDevitt et al, 1995, Mol. Microbiol. 16, 895-907) has shown that region A of ClfA is sufficient for the clumping phenotype.

However, previously, no one has been able to generate monoclonal antibodies to the *S. aureus* ClfA protein. Accordingly, the present invention relates to an isolated and/or purified monoclonal antibody which can bind to the ClfA protein or its binding subdomains, including the Clf40, Clf33 and ClfA N3 proteins, and which thus can be useful in methods of preventing and treating staphylococcal infection when used in amounts effective to prevent or treat such infections. These monoclonal antibodies may be produced using, e.g., the method of Kohler and Milstein, Nature 256:495-497 (1975), or other suitable ways known in the field, and in addition can be prepared as chimeric, humanized, or human monoclonal antibodies in ways that would be well known in this field. Still further, monoclonal antibodies may be prepared from a single chain, such as the light or heavy chains, and in addition may be prepared from active fragments of an antibody which retain the binding characteristics (e.g., specificity and/or affinity) of the whole antibody. By active fragments is meant an antibody fragment which has the same binding specificity as a complete antibody which binds to the ClfA protein, and the term "antibody" as used herein is meant to include said fragments. Additionally, antisera prepared using monoclonal or polyclonal antibodies in accordance with the invention are also contemplated and may be prepared in a number of suitable ways as would be recognized by one skilled in the art.

As indicated above, antibodies to ClfA may be prepared in a number of suitable ways that would be well known in the art, such as the well-established Kohler and Milstein method described above which can be utilized to generate monoclonal antibodies. In one such method, mice are injected intraperitoneally once a week for a prolonged period with a purified recombinant ClfA protein, or isolated subdomain protein such as Clf40, Clf33, or ClfA N3, or an active portion thereof, followed by a test of blood obtained from the immunized mice to determine reactivity to the purified ClfA. Following identification of mice reactive to ClfA, lymphocytes isolated from mouse spleens are fused to mouse myeloma cells to produce hybridomas positive for the antibodies against ClfA which are then isolated and cultured, following by purification and isotyping.

In order to generate monoclonal antibodies in accordance with the invention, it is thus preferred that these be generated using recombinantly prepared ClfA, Clf40, Clf33 or N3 proteins using conventional methods well known in the art. For example, one such method employs the use of *E. coli* expression vector pQE-30 as an expression vector for cloning and expressing recombinant proteins and peptides.

Using PCR, the A domain of ClfA (Clf40 representing M 40-559 or Clf33 representing AA 221-550) was amplified from *S. aureus* Newman genomic DNA and subcloned into the *E. coli* expression vector pQE-30 (Qiagen), which allows for the expression of a recombinant fusion protein containing six histidine residues. This vector was subsequently transformed into the *E. coli* strain ATCC 55151, grown in a 15-liter fermentor to an optical density ($OD_{600}$) of 0.7 and induced with 0.2 mM isopropyl-1-beta-D galactoside (IPTG) for 4 hours. The cells were harvested using an AG Technologies hollow-fiber assembly (pore size of 0.45 μm) and the cell paste frozen at −80° C. Cells were lysed in 1×PBS (10 mL of buffer/1 g of cell paste) using 2 passes through the French Press @ 1100 psi. Lysed cells were spun down at 17,000 rpm for 30 minutes to remove cell debris. Supernatant was passed over a 5-mL HiTrap Chelating (Pharmacia) column charged with 0.1M $NiCl_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 200 mM imidazole (Buffer B) over 30 column volumes. Clf40 or Clf33 eluted at ~13% Buffer B (~26 mM imidazole). Absorbance at 280 nm was monitored. Fractions containing Clf40 or Clf33 were dialyzed in 1×PBS.

The protein was then put through an endotoxin removal protocol. Buffers used during this protocol were made endotoxin free by passing over a 5-mL Mono-Q sepharose (Pharmacia) column. Protein was divided evenly between 4×15 mL tubes. The volume of each tube was brought to 9 mL with Buffer A. 1 mL of 10% Triton X-114 was added to each tube and incubated with rotation for 1 hour at 4° C. Tubes were placed in a 37° C. water bath to separate phases. Tubes were spun down at 2,000 rpm for 10 minutes and the upper aqueous phase from each tube was collected and the detergent extraction repeated. Aqueous phases from the 2nd extraction were combined and passed over a 5-mL IDA chelating (Sigma) column, charged with 0.1M $NiCl_2$ to remove remaining detergent. The column was washed with 9 column volumes of Buffer A before the protein was eluted with 3 column volumes of Buffer B. The eluant was passed over a 5-mL Detoxigel (Sigma) column and the flow-through collected and reapplied to the column. The flow-through from the second pass was collected and dialyzed in 1×PBS. The purified product was analyzed for concentration, purity and endotoxin level before administration into the mice.

The amino acid sequence for Clf40 obtained in this manner is shown herein as SEQ ID NO:2, and is encoded by nucleic acids having the sequence as set forth in SEQ ID NO:1, or degenerates thereof. In addition, the amino acid sequence for Clf33 obtained in this manner is shown herein as SEQ ID NO:4, and is encoded by nucleic acids having the sequence as set forth in SEQ ID NO:3, or degenerates thereof.

In accordance with the invention, following isolation of the ClfA protein or its active subdomains such as Clf40, Clf33 or ClfA N3, monoclonal antibodies to these proteins can be produced by a number of suitable ways. For example, in one preferred method, the purified Clf40 and Clf33 proteins were used to generate a panel of murine monoclonal antibodies. Briefly, a group of Balb/C mice received a series of subcutaneous immunizations of 50 □g of Clf40 or Clf33 protein in solution or mixed with adjuvant as described below:

| Injection | Day | Amount (μg) | Route | Adjuvant |
|---|---|---|---|---|
| Primary | 0 | 50 | Subcutaneous | Freund's Complete |
| Boost #1 | 14 | 5 (Clf40) 10 (Clf33) | Intravenous | PBS |

Three days after the final boost, the spleens were removed, teased into a single cell suspension and the lymphocytes harvested. The lymphocytes were then fused to a SP2/0-Ag14 myeloma cell line (ATCC #1581). Cell fusion, subsequent plating and feeding were performed according to the Production of Monoclonal Antibodies protocol from *Current Protocols in Immunology* (Chapter 2, Unit 2.).

Any clones that were generated from the fusion were then screened for specific anti-Clf40 antibody production using a standard ELISA assay. Positive clones were expanded and tested further. Fifteen positive clones were originally identified and cloned by limiting dilution for further characterization. Single cell clones were tested for activity in a direct binding ELISA, a modified ELISA to measure inhibition of fibrinogen binding to CLF40, whole bacterial cell binding by flow cytometry and affinity for Clf40 binding by Biacore analysis.

*S. aureus* bacterial samples (strains Barnett, 67-0, ATCC#25923 and ATCC#49230) were collected, washed and incubated with Mab 13-2, 12-9, 13-1 or PBS alone (control) at a concentration of 2 mg/ml after blocking protein A sites with rabbit IgG (50 mg/ml). Following incubation with antibody, bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured.

High binding 96 well plates were coated with 1 mg/ml solution of Clf40 in PBS (pH 7.4), covered, and incubated at room temperature for 2 hours. Plates were then washed with PBS, 0.05% Tween 20 and blocked with 1% BSA solution for 1 hour at room temperature. Following washing, monoclonal antibody supernatant was added and plates were incubated for 1 hour at room temperature. Plates were then washed and 0.1 mg/ml human fibrinogen solution was added to each well. Plates were incubated for 1 hour at room temperature and washed. Sheep anti-fibrinogen AP conjugate was added at a 1:750 dilution in PBS, 0.05% Tween 20, 0.1% BSA and allowed to incubate for 1 hour at room temperature. Plates were then washed and pNPP (developing solution) was added at a final concentration of 1 mg/ml. Plates were incubated 15-30 minutes at 37° C. and results were read at 405 nm and analyzed using Perkin Elmer HTS 7000 Bio-Assay reader.

Kinetic analysis was performed on a Biacore 3000 using the Ligand capture method included in the software. A rabbit anti-mouse-Fc antibody (Biacore) was amine coupled to a CM5 chip. The monoclonal antibody being analyzed was then passed over the chip, allowing binding to the Fc portion. Varying concentrations of the Clf40 or Clf33 protein were then passed over the chip surface and data collected. Using the Biacore provided Evaluation software (Version 3.1), $k_{on}$ and $k_{off}$ were measured and $K_A$ and $K_D$ were calculated.

As shown in data below, immunizations to generate monoclonal antibodies in accordance with the present invention directed to Clf40 or active portions of Clf40 (N2N3 or N3 regions) have yielded monoclonal antibodies with different and diverse reactivity and cross-reactivity profiles.

Although production of antibodies using recombinant forms of the ClfA protein is preferred, antibodies may be generated from natural isolated and purified ClfA proteins or regions as well, and monoclonal or polyclonal antibodies can be generated using the natural ClfA proteins or active regions in the same manner as described above to obtain such antibodies. Still other conventional ways are available to generate the ClfA antibodies of the present invention using recombinant or natural purified ClfA proteins or its active regions, as would be recognized by one skilled in the art.

As would be recognized by one skilled in the art, the antibodies of the present invention may also be formed into suitable pharmaceutical compositions for administration to a human or animal patient in order to treat or prevent an infection caused by staphylococcal bacteria. Pharmaceutical compositions containing the antibodies of the present invention, or effective fragments thereof, may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of antibody compositions, and other information concerning compositions, methods and applications with regard to other MSCRAMMT™ will generally also be applicable to the present invention involving antibodies to the ClfA MSCRAMM™ and are disclosed, for example, in U.S. Pat. No. 6,288,214 (Hook et al.), incorporated herein by reference.

The antibody compositions of the present invention which are generated against the ClfA protein or its effective subdomains such as Clf40, Clf33 or N3 may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, RIBBI adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as Novasome™ lipid vesicles (Micro Vescular Systems, Inc., Nashua, N.H.) may also be useful.

In any event, the antibody compositions of the present invention will thus be useful for interfering with, modulating, inhibiting binding interactions between ClfA on staphylococcal bacteria and fibrinogen on host cells and tissues, or in displacing staphylococcal bacteria which has become bound to fibrinogen associated with host cells and tissues. Accordingly, the present invention will have particular applicability in developing compositions and methods of preventing or treating staphylococcal infection, and in inhibiting binding of staphylococcal bacteria to host tissue and/or cells.

In accordance with the present invention, methods are provided for preventing or treating a staphylococcal infection which comprise administering an effective amount of an antibody to the ClfA protein or its active subregions such as Clf40, Clf33 or N3 as described above in amounts effective to treat or prevent the infection. In addition, these monoclonal antibodies have been shown to be useful in impairing the binding of staphylococcal bacteria to fibrinogen or fibrin, and have thus proved effective in treating or preventing infection from staph bacteria such as *S. aureus*. Even further, the antibodies in accordance with the invention are doubly effective in that they have been shown to be cross-reactive across a wide variety of *S. aureus* strains which will thus improve the effectiveness and efficiency of compositions based on the monoclonals of the present invention.

Accordingly, in accordance with the invention, administration of the antibodies of the present invention in any of the conventional ways described above (e.g., topical, parenteral, intramuscular, etc.), and will thus provide an extremely useful method of treating or preventing staphylococcal infections in human or animal patients. By effective amount is meant that level of use, such as of an antibody titer, that will be sufficient to either prevent adherence of the bacteria, to inhibit binding of staph bacteria to host cells and thus be useful in the treatment or prevention of a staph infection. As would be recognized by one of ordinary skill in this art, the level of antibody titer needed to be effective in treating or preventing staphylococcal infection will vary depending on the nature and condition of the patient, and/or the severity of the pre-existing staphylococcal infection.

In addition to the use of antibodies to the ClfA protein and the regions in the A domain of that protein to treat or prevent *S. aureus* infection as described above, the present invention contemplates the use of these antibodies in a variety of ways, including the detection of the presence of *S. aureus* to diagnose a staph infection, whether in a patient or on medical equipment which may also become infected. In accordance with the invention, a preferred method of detecting the presence of staph infections involves the steps of obtaining a sample suspected of being infected by one or more staphylococcal bacteria species or strains, such as a sample taken from an individual, for example, from one's blood, saliva, tissues, bone, muscle, cartilage, or skin. The cells can then be lysed, and the DNA extracted, precipitated and amplified. Following isolation of the sample, diagnostic assays utilizing the antibodies of the present invention may be carried out to detect the presence of *S. aureus*, and such assay techniques for determining such presence in a sample are well known to those skilled in the art and include methods such as radioimmunoasssay, Western blot analysis and ELISA assays. In general, in accordance with the invention, a method of diagnosing an *S. aureus* infection is contemplated wherein a sample suspected of being infected with *S. aureus* infection has added to it a ClfA protein antibody in accordance with the present invention, and *S. aureus* is indicated by antibody binding to the ClfA proteins in the sample.

Accordingly, antibodies in accordance with the invention may be used for the specific detection of staphylococcal map proteins, for the prevention of infection from staph bacteria, for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies to the ClfA proteins, including the products of an Fab immunoglobulin expression library. Accordingly, the invention contemplates the use of single chains such as the variable heavy and light chains of the antibodies as will be set forth below. Generation of any of these types of antibodies or antibody fragments is well known to those skilled in the art. In the present case, monoclonal antibodies to ClfA proteins have been generated and isolated and shown to protect against staphylococcal infection.

Any of the above described antibodies may be labeled directly with a detectable label for identification and quantification of staph bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies to ClfA as described above may also be used in production facilities or laboratories to isolate additional quantities of the proteins, such as by affinity chromatography. For example, the antibodies of the invention may also be utilized to isolate additional amounts of the ClfA protein or its active fragments.

The isolated antibodies of the present invention, or active fragments thereof, may also be utilized in the development of vaccines for passive immunization against staph infections. Further, when administered as pharmaceutical composition to a wound or used to coat medical devices or polymeric biomaterials in vitro and in vivo, the antibodies of the present invention, may be useful in those cases where there is a previous staph infection because of the ability of this antibody to further restrict and inhibit *S. aureus* binding to fibrinogen or fibrin and thus limit the extent and spread of the infection. In addition, the antibody may be modified as necessary so that, in certain instances, it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., *Nature* 321:522-525 (1986) or Tempest et al. *Biotechnology* 9:266-273 (1991) or "veneered" by changing the surface exposed murine framework residues in the immunoglobulin variable regions to mimic a homologous human framework counterpart as described, e.g., by Padlan, Molecular Imm. 28:489-498 (1991), these references incorporated herein by reference. Even further, when so desired, the monoclonal antibodies of the present invention may be administered in conjunction with a suitable antibiotic to further enhance the ability of the present compositions to fight bacterial infections.

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or active fragment, or pharmaceutical composition derived therefrom, to a surface of the device, preferably an outer surface that would be exposed to streptococcal bacterial infection. The surface of the device need not be entirely covered by the protein, antibody or active fragment.

In a preferred embodiment, the antibodies may also be used as a passive vaccine which will be useful in providing suitable antibodies to treat or prevent a staphylococcal infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable carrier to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a staphylococcal infection, and one would readily recognize that this amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. As will be pointed out below, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S) mercury sodium salt) (Sigma Chemical Company, St. Louis, Mo.).

When used with suitable labels or other appropriate detectable biomolecule or chemicals; the monoclonal antibodies described herein are useful for purposes such as in vivo and in vitro diagnosis of staphylococcal infections or detection of staphylococcal bacteria. Laboratory research may also be facilitated through use of such antibodies. Various types of labels and methods of conjugating the labels to the antibodies of the invention are well known to those skilled in the art, such as the ones set forth below.

For example, the antibody can be conjugated (directly or via chelation) to a radiolabel such as, but not restricted to, $^{32}P$, $^{3}H$, $^{14}C$, $^{35}S$, $^{125}I$, or $^{131}I$. Detection of a label can be by methods such as scintillation counting, gamma ray spectrometry or autoradiography. Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The location of a ligand in cells can be determined by labeling an antibody as described above and detecting the label in accordance with methods well known to those skilled in the art, such as immunofluorescence microscopy using procedures such as those described by Warren and Nelson (*Mol. Cell. Biol.*, 7: 1326-1337, 1987).

As indicated above, the monoclonal antibodies of the present invention, or active portions or fragments thereof, are particularly useful for interfering with the initial physical interaction between a staphylococcal pathogen responsible for infection and a mammalian host, such as the adhesion of the bacteria to mammalian extracellular matrix proteins such as fibrinogen, and this interference with the physical interaction may be useful both in treating patients and in preventing or reducing bacteria infection on in-dwelling medical devices to make them safer for use.

In another embodiment of the present invention, a kit which may be useful in isolating and identifying staphylococcal bacteria and infection is provided which comprises the antibodies of the present invention in a suitable form, such as lyophilized in a single vessel which then becomes active by addition of an aqueous sample suspected of containing the staphylococcal bacteria. Such a kit will typically include a suitable container for housing the antibodies in a suitable form along with a suitable immunodetection reagent which will allow identification of complexes binding to the ClfA antibodies of the invention. For example, the immunodetection reagent may comprise a suitable detectable signal or label, such as a biotin or enzyme that produces a detectable color, etc., which normally may be linked to the antibody or which can be utilized in other suitable ways so as to provide a detectable result when the antibody binds to the antigen.

In short, the antibodies of the present invention which bind to the ClfA protein or active fragments thereof are thus extremely useful in treating or preventing staphylococcal infections in human and animal patients and in medical or other in-dwelling devices. Accordingly, the present invention relates to methods of identifying and isolating antibodies which can bind to ClfA and which can be used in methods of treatment of staph infections which involve opsonophagocytic killing of the bacteria. Antibodies which are identified and/or isolated using the present method, such as the ClfA antibody which can bind the ClfA protein and which can prevent or treat a staph infection thus is part of the present invention

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation and Sequencing of Clf40 and Clf33

Using PCR, the A domain of ClfA (Clf40 representing M 40-559 or Clf33 representing M 221-550) was amplified from *S. aureus* Newman genomic DNA and subcloned into the *E. coli* expression vector PQE-30 (Qiagen), which allows for the expression of a recombinant fusion protein containing six histidine residues. This vector was subsequently transformed into the *E. Coli* strain ATCC 55151, grown in a 15-liter fermentor to an optical density ($OD_{600}$) of 0.7 and induced with 0.2 mM isopropyl-1-beta-D galactoside (IPTG) for 4 hours. The cells were harvested using an AG Technologies hollow-fiber assembly (pore size of 0.45 µm) and the cell paste frozen at −80° C. Cells were lysed in 1×PBS (10 mL of buffer/1 g of cell paste) using 2 passes through the French Press @ 1100 psi. Lysed cells were spun down at 17,000 rpm for 30 minutes to remove cell debris. Supernatant was passed over a 5-mL HiTrap Chelating (Pharmacia) column charged with 0.1M $NiCl_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 200 mM imidazole (Buffer B) over 30 column volumes. Clf40 or Clf33 eluted at ~13% Buffer B (~26 mM imidazole). Absorbance at 280 nm was monitored. Fractions containing Clf40 or Clf33 were dialyzed in 1×PBS.

The protein was then put through an endotoxin removal protocol. Buffers used during this protocol were made endotoxin free by passing over a 5-mL Mono-Q sepharose (Pharmacia) column. Protein was divided evenly between 4×15 mL tubes. The volume of each tube was brought to 9 mL with Buffer A. 1 mL of 10% Triton X-114 was added to each tube and incubated with rotation for 1 hour at 4° C. Tubes were placed in a 37° C. water bath to separate phases. Tubes were spun down at 2,000 rpm for 10 minutes and the upper aqueous phase from each tube was collected and the detergent extraction repeated. Aqueous phases from the 2nd extraction were combined and passed over a 5-mL IDA chelating (Sigma) column, charged with 0.1M $NiCl_2$ to remove remaining detergent. The column was washed with 9 column volumes of Buffer A before the protein was eluted with 3 column volumes of Buffer B. The eluant was passed over a 5-mL Detoxigel (Sigma) column and the flow-through collected and reapplied to the column. The flow-through from the second pass was collected and dialyzed in 1×PBS. The purified product was analyzed for concentration, purity and endotoxin level before administration into the mice.

The protein and nucleic acid sequences are included below. The Clf40 amino acid sequence is included below as SEQ ID NO:2, and this is coded for by the nucleic acid sequence SEQ ID NO:1, and would also be coded by degenerates thereto. The Clf33 amino acid sequence is included below as SEQ ID NO:4, and this is coded for by the nucleic acid sequence SEQ ID NO:3, and would also be coded by degenerates thereto.

Example 2

Monoclonal Antibody Production Using Clf40 and Clf33

The purified Clf40 or Clf33 protein was used to generate a panel of murine monoclonal antibodies. Briefly, a group of Balb/C mice received a series of subcutaneous immunizations of 50 µg of Clf40 or Clf33 protein in solution or mixed with adjuvant as described below in Table I:

TABLE I

| Injection | Day | Amount (µg) | Route | Adjuvant |
|---|---|---|---|---|
| Primary | 0 | 50 | Subcutaneous | Freund's Complete |
| Boost #1 | 14 | 5 (Clf40) 10 (Clf33) | Intravenous | PBS |

Three days after the final boost, the spleens were removed, teased into a single cell suspension and the lymphocytes harvested. The lymphocytes were then fused to a SP2/0-Ag14 myeloma cell line (ATCC #1581). Cell fusion, subsequent plating and feeding were performed according to the Production of Monoclonal Antibodies protocol from *Current Protocols in Immunology* (Chapter 2, Unit 2.).

Any clones that were generated from the fusion were then screened for specific anti-Clf40 antibody production using a standard ELISA assay. Positive clones were expanded and tested further. Fifteen positive clones were originally identified and cloned by limiting dilution for further characterization. Single cell clones were tested for activity in a direct binding ELISA, a modified ELISA to measure inhibition of fibrinogen binding to CLF40, whole bacterial cell binding by flow cytometry and affinity for Clf40 binding by Biacore analysis. Test results are include in Table II below:

TABLE II

| ClfA Monoclonal Antibody | Binding Kinetics | Inhibition of Fbg binding | Binding to *S. aureus* Barnett | Binding to *S. aureus* 67-0 | Binding to *S. aureus* ATCC #25923 | Binding to *S. aureus* ATCC #49230 |
|---|---|---|---|---|---|---|
| F12-9 | $k_{on}$ 7.74 × $10^5$ $k_{off}$ 4.46 × $10^{-4}$ $K_D$ 5.76 × $10^{-10}$ | 50-70% | 72% | 62% | 60% | 94% |
| F13-1 | $k_{on}$ 1.11 × $10^5$ $k_{off}$ 6.13 × $10^{-3}$ $K_D$ 5.51 × $10^{-8}$ | 0-15% | — | — | — | 9% |
| F13-2 | $k_{on}$ 1.19 × $10^5$ $k_{off}$ 2.81 × $10^{-4}$ $K_D$ 2.35 × $10^{-9}$ | 40-60% | 59% | 65% | 55% | 93% |

Binding to Whole Bacteria

*S. aureus* bacterial samples (strains Barnett, 67-0, ATCC#25923 and ATCC#49230) were collected, washed and incubated with Mab 13-2, 12-9, 13-1 or PBS alone (control) at a concentration of 2 mg/ml after blocking protein A sites with rabbit IgG (50 mg/ml). Following incubation with antibody, bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured.

Inhibition (ELISA)

High binding 96 well plates were coated with 1 µg/ml solution of Clf40 in PBS (pH 7.4), covered, and incubated at room temperature for 2 hours. Plates were then washed with PBS, 0.05% Tween 20 and blocked with 1% BSA solution for 1 hour at room temperature. Following washing, monoclonal antibody supernatant was added and plates were incubated for 1 hour at room temperature. Plates were then washed and 0.1 mg/ml human fibrinogen solution was added to each well. Plates were incubated for 1 hour at room temperature and washed. Sheep anti-fibrinogen AP conjugate was added at a 1:750 dilution in PBS, 0.05% Tween 20, 0.1% BSA and allowed to incubate for 1 hour at room temperature. Plates were then washed and pNPP (developing solution) was added at a final concentration of 1 mg/ml. Plates were incubated 15-30 minutes at 37° C. and results were read at 405 nm and analyzed using Perkin Elmer HTS 7000 Bio-Assay reader.

Kinetic Analysis

Kinetic analysis was performed on a Biacore 3000 using the Ligand capture method included in the software. A rabbit anti-mouse-Fc antibody (Biacore) was amine coupled to a CM5 chip. The monoclonal antibody being analyzed was then passed over the chip, allowing binding to the Fc portion. Varying concentrations of the Clf40 or Clf33 protein were then passed over the chip surface and data collected. Using the Biacore provided Evaluation software (Version 3.1), $k_{on}$ and $k_{off}$ were measured and $K_A$ and $K_D$ were calculated.

Example 3

Additional Studies of Clf40 and Clf33

Using PCR, the A domain of ClfA (Clf40 representing M 40-559, Clf33-N2N3 domain representing AA 221-550 or Clf-N3 domain representing AA370-559) was amplified from *S. aureus* Newman genomic DNA and subcloned into the *E. coli* expression vector PQE-30 (Qiagen), which allows for the expression of a recombinant fusion protein containing six histidine residues. This vector was subsequently transformed into the *E. coli* strain ATCC 55151, grown in a 15-liter fermentor to an optical density ($OD_{600}$) of 0.7 and induced with 0.2 mM isopropyl-1-beta-D galactoside (IPTG) for 4 hours. The cells were harvested using an AG Technologies hollow-fiber assembly (pore size of 0.45 mm) and the cell paste frozen at −80° C. Cells were lysed in 1×PBS (10 mL of buffer/1 g of cell paste) using 2 passes through the French Press @ 1100 psi. Lysed cells were spun down at 17,000 rpm for 30 minutes to remove cell debris. Supernatant was passed over a 5-mL HiTrap Chelating (Pharmacia) column charged with 0.1M $NiCl_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 200 mM imidazole (Buffer B) over 30 column volumes. Clf protein was eluted at ~13% Buffer B (~26 mM imidazole). Absorbance at 280 nm was monitored. Fractions containing Clf40 or Clf33 were dialyzed in 1×PBS.

The protein was then put through an endotoxin removal protocol. Buffers used during this protocol were made endotoxin free by passing over a 5-mL Mono-Q sepharose (Pharmacia) column. Protein was divided evenly between 4×15 mL tubes. The volume of each tube was brought to 9 mL with Buffer A. 1 mL of 10% Triton X-114 was added to each tube and incubated with rotation for 1 hour at 4° C. Tubes were placed in a 37° C. water bath to separate phases. Tubes were spun down at 2,000 rpm for 10 minutes and the upper aqueous phase from each tube was collected and the detergent extraction repeated. Aqueous phases from the 2nd extraction were combined and passed over a 5-mL IDA chelating (Sigma) column, charged with 0.1M $NiCl_2$ to remove remaining detergent. The column was washed with 9 column volumes of Buffer A before the protein was eluted with 3 column volumes of Buffer B. The eluant was passed over a 5-mL Detoxigel (Sigma) column and the flow-through collected and reapplied to the column. The flow-through from the second pass was collected and dialyzed in 1×PBS. The purified product was analyzed for concentration, purity and endotoxin level before administration into the mice.

Monoclonal Antibody Production

The purified Clf40, Clf33 or N3 protein was used to generate a panel of murine monoclonal antibodies. Briefly, a group of Balb/C or SJL mice received a series of subcutaneous immunizations of 1-10 mg of protein in solution or mixed with adjuvant as described below in Table III:

TABLE III

| | Day | Amount (mg) | Route | Adjuvant |
|---|---|---|---|---|
| RIMMS Injection | | | | |
| #1 | 0 | 5 | Subcutaneous | FCA/RIBI |
| #2 | 2 | 1 | Subcutaneous | FCA/RIBI |
| #3 | 4 | 1 | Subcutaneous | FCA/RIBI |
| #4 | 7 | 1 | Subcutaneous | FCA/RIBI |
| #5 | 9 | 1 | Subcutaneous | FCA/RIBI |
| Conventional Injection | | | | |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice (RIMMS) or seven days after a boost (conventional) serum was collected and titered in ELISA assays against MSCRAMMs or on whole cells (*S. aureus* and *S. epidermidis*). Three days after the final boost, the spleens or lymph nodes were removed, teased into a single cell suspension and the lymphocytes harvested. The lymphocytes were then fused to a SP2/0-Ag14 myeloma cell line (ATCC #1581). Cell fusion, subsequent plating and feeding were performed according to the Production of Monoclonal Antibodies protocol from *Current Protocols in Immunology* (Chapter 2, Unit 2.).

Any clones that were generated from the fusion were then screened for specific anti-Clf40, SdrG or FnbpA antibody production using a standard ELISA assay. Positive clones were expanded and tested further. Candidates were further tested for activity in a direct binding ELISA, a modified ELISA to measure inhibition of fibrinogen binding to CLF40, whole bacterial cell binding by flow cytometry and Clf40 binding/inhibition of fibrinogen-Clf40 binding by Biacore analysis.

Biacore Analysis

Throughout the analysis, the flow rate remained constant at 10 ml/min. Prior to the ClfA 40 injection, test antibody was adsorbed to the chip via RAM-Fc binding. At time 0, ClfA 40 at a concentration of 30 mg/ml was injected over the chip for 3 min followed by 2 minutes of dissociation. This phase of the analysis measured the relative association and disassociation kinetics of the Mab/ClfA interaction. In the second phase of the analysis, the ability of the Mab bound ClfA to interact and bind fibrinogen was measured. Fibrinogen at a concentration of 100 mg/ml was injected over the chip and after 3 minutes a report point is taken.

Binding to Whole Bacteria

Bacterial samples (Newman) were collected, washed and incubated with Mab or PBS alone (control) at a concentration of 2 mg/ml after blocking protein A sites with rabbit IgG (50 mg/ml). Following incubation with antibody, bacterial cells were incubated with Goat-$F_{(ab')_2}$-Anti-Mouse-$F_{(ab')_2}$-FITC which served as the detection antibody. After antibody labeling, bacterial cells were aspirated through the FACS-caliber flow cytometer to analyze fluorescence emission (excitation: 488, emission: 570). For each bacterial strain, 10,000 events were collected and measured.

Inhibition (ELISA)

High binding 96 well plates were coated with 1 ug/ml solution of Clf40 in PBS (pH 7.4), covered, and incubated at room temperature for 2 hours. Plates were then washed with PBS, 0.05% Tween 20 and blocked with 1% BSA solution for 1 hour at room temperature. Following washing, monoclonal antibody supernatant was added and plates were incubated for 1 hour at room temperature. Plates were then washed and 0.1 mg/ml human fibrinogen solution was added to each well. Plates were incubated for 1 hour at room temperature and washed. Sheep anti-fibrinogen AP conjugate was added at a 1:750 dilution in PBS, 0.05% Tween 20, 0.1% BSA and allowed to incubate for 1 hour at room temperature. Plates were then washed and pNPP (developing solution) was added at a final concentration of 1 mg/ml. Plates were incubated 15-30 minutes at 37° C. and results were read at 405 nm and analyzed using Perkin Elmer HTS 7000 Bio-Assay reader.

Example 4

Immunization with all or Portions of Clf40 Generate Monoclonal Antibodies with Different Reactivity Patterns Table IV below shows the results of immunization tests with the active regions of the present invention, including Clf40, Clf33 (which constitutes the N2N3 region of the ClfA A domain), and the ClfA N3 region alone.

The results displayed in this table show that immunizations to generate monoclonal antibodies with Clf40 or portions of Clf40 (N2N3 or N3) yield monoclonal antibodies with broad and diverse reactivity profiles and which exhibit substantial cross-reactivity across a wide variety of staphylococcal strains.

Example 5

Use of the Biacore to Select High Affinity Mabs that Block ClfA Binding to Fibrinogen Biacore Analysis Throughout the experiment represented in FIG. 1, the flow rate remained constant at 10 ml/min. Prior to the ClfA 40 injection, 946 RU of Mab 13-1 and 768 RU of Mab 13-2 were adsorbed to the chip via RAM-Fc binding. At time 0 on the graph, ClfA 40 at a concentration of 30 mg/ml was injected over the chip for 3 min followed by 2 minutes of dissociation. The 13-1 Mab bound 58 RU of ClfA and the 13-2 Mab bound 168 RU of ClfA at the end of the ClfA injection time. This phase of the experiment measured the relative association and disassociation kinetics of the Mab/ClfA interaction. In the second phase of the experiment measures the ability of the Mab bound ClfA to interact and bind fibrinogen. Fibrinogen at a concentration of 100 mg/ml was injected over the chip and after 3 minutes 64 RU of fibrinogen bound to the ClfA bound to Mab 13-1 but 0 RUs of fibrinogen bound to the ClfA bound to Mab 13-2.

TABLE IV

| | | | Reactivity | | | | | | |
|---|---|---|---|---|---|---|---|---|---|
| | | | ELISA | | | Biacore | | Flow | |
| Antigen | Fusion | Monoclonal | Clf40 | SdrG | FnbpA | Binding | Inhibition | Cytometry | Inhibition | FYI |
| ClfA N3 | RIMMS | F29-19 | Y | N | N | N | N | nt | nt | |
| Includes following: | | F29-71 | Y | N | N | N | N | nt | nt | |
| F29 F30 F31 F32 | | F29-92 | Y | N | N | N | N | nt | nt | |
| F34 F36 | | F31-20 | Y | N | N | N | N | nt | nt | |
| | | F31-36 | Y | N | N | N | N | nt | nt | |
| | | F31-100 | Y | N | N | N | N | nt | nt | |
| | | F31-195 | Y | N | N | N | N | nt | nt | |
| | | F32-22 | Y | N | N | N | N | nt | nt | |
| | | F34-15 | Y | N | N | N | N | nt | nt | |
| | | F36-77 | Y | N | N | N | N | nt | nt | |
| | | F36-197 | Y | N | N | N | N | nt | nt | |
| ClfA N2N3 (Clf33) | Conventional | INH-M010001 | Y | N | N | Y | N | Y | Y | 12-9 |
| Includes following: | | F12-3 | Y | nt | nt | Y | nt | Y | N | |
| F11 F12 F17 F18 | | F12-1 | Y | nt | nt | Y | nt | Y | N | |
| | | F12-5 | Y | nt | nt | Y | nt | Y | N | |
| | | F12-10 | Y | nt | nt | Y | nt | Y | Y | |
| ClfA N2N3 (Clf33) | RIMMS | F33-7 | Y | N | N | Y | Y | Y | nt | |
| Includes following: | | F35-279 | Y | N | N | Y | Y | N | nt | |
| F33 F35 F38 F40 | | F35-177 | Y | N | N | Y | N | Y | nt | |
| | | F40-7 | Y | N | N | Y | Y | Y | nt | |
| | | F38-300 | Y | N | N | Y | Y | N | nt | |
| | | F35-129 | Y | N | N | N | N | nt | nt | |
| Clf40 | Conventional | INH-M000030 | Y | nt | nt | Y | N | Y | Y | 13-2 |
| Includes following: | | INH-M010004 | Y | nt | nt | Y | N | Y | N | 15-EC6 |
| F13 F14 F15 F16 | | INH-M010003 | Y | nt | nt | Y | N | N | N | 13-1 |
| | | F13-6 | Y | nt | nt | Y | nt | Y | Y | |

Y = a positive result
N = a negative result
nt = not tested

Example 6

Comparison of Mab 13-2 against *S. aureus* strain Barnett and *S. aureus* ATCC 25923

Antibody Scale-up and Purification

Hybridoma cells were grown in RPMI/DMEM, 1× Nutridoma-SP media containing 2 mM sodium pyruvate, 4 mM L-glutamine and 2× penicillin-streptomycin to 2-3 liter culture volumes. Hybridoma supernatants were then harvested by centrifugation. The supernatants were filtered through 0.45 µM filters and the IgG was affinity purified using protein G chromatography. The monoclonal antibodies were eluted using 0.1M glycine, pH 2.7 and immediately neutralized with one-tenth volume of 2M Tris, pH 8.0. The purified IgG was then dialyzed against 1× D-phosphate buffered saline, pH 7.4. If needed, the purified antibody was concentrated and aliquots frozen.

*Staphylococcus Aureus* Strains

*S. aureus* cells were taken from a frozen glycerol stock and were inoculated onto a single blood agar plate and grown for 24 hours at 37° C. Single colonies were then transferred to new blood agar plates. Eighty plates were inoculated to prepare 50 mls of final frozen stock. The plates were then incubated for 24 hours at 37° C. Following incubation, the colonies were scraped off the surface of each plate into four 50 ml tubes containing 10 mls of 1×PBS (20 plates per tube) while gently vortexing to remove the bacteria from the scraper. An additional 10 mls of 1×PBS was then added to the 10 mls of bacterial suspension, while vigorously vortexing to facilitate separation of any agar debris from the bacteria. The suspension was pelleted by centrifugation, 3500×g at 4° C. for 10 minutes. The bacteria was washed in D-PBS and resuspended in 50 mls of freezing media. The bacterial stock was placed into 1 ml aliquots by snap freezing in an ethanol/dry ice bath and placed in a −80° C. freezer. The concentration (CFU/ml) of the frozen stock was determined by thawing 1 ml aliquot of stock, and preparing serial dilutions from $10^{-5}$ to $10^{-11}$. Dilutions were plated in duplicate on blood agar plates and incubated for 37° C. for 16-18 hours. The CFU/ml was determined (CFU/ml=(average # colonies X dilution factor)/0.050 mls) and averaged for each dilution to determine the average CFU/ml. On the day of injection, aliquots of each strain were thawed, combined into one tube per strain, and vortexed.

Animal, Sex, Species, Number, Age and Source

Female Balb/C mice (5-6 weeks of age) were purchased from Taconic Quality Laboratory Animals and Services for Research (Germantown, N.Y.). Animals were allowed to acclimate for at least 14 days prior to initiation of treatment. Upon arrival, the mice were examined, group housed (5/cage) in polycarbonate shoe box cages with absorbent bedding. All mice were placed on a 12 hour light-dark cycle under the required husbandry standards found in the NIH Guide for the Care and Use of Laboratory Animals.

Identification and Randomization

All animals were uniquely identified using tail tattoos prior to dosing. Prior to initiation of treatment, the animals were individually weighed and their health was evaluated. Mice were randomized and assigned to treatment groups using stratified body weights.

ClfA Specific Monoclonal Antibodies (Mab), Isotype

ClfA specific murine monoclonal antibodies were isotyped using Becton Dickenson Cytometric Bead Array for Murine Isotyping. Isotype was determined using flow cytometry according to the manufacturers protocol.

13-1 Clf40 Mab, $IgG_1$
13-2 Clf40 Mab, $IgG_1$
12-9 Clf33 Mab, $IgG_1$

Controls

ATTC 1771, $IgG_1$

Phosphate Buffered Saline, pH 7.4 (PBS) was purchased from Life Technologies, Inc. (Cat. No. 10010-023; Lot No. 1078749).

Experimental Design

TABLE V

| Group # | No. of Mice | TREATMENT | | | | | CHALLENGE | | |
|---|---|---|---|---|---|---|---|---|---|
| | | Antibody | Dose | Route | Frequency | Time Point | Bacteria | Stock Dilution. | Volume/ Route |
| 1 | 12 | 13-2 | 36 mg/kg | i.p. | Once | −18 hr. | ATCC 25923 | 1:20 | 0.1 ml/IV |
| 2 | 15 | CRL1771 | 36 mg/kg | | | | ATCC 25923 | 1:20 | |
| 3 | 15 | D-PBS | N/A | | | | ATCC 25923 | 1:20 | |
| 4 | 12 | 13-2 | 36 mg/kg | | | | Barnett | 1:20 | |
| 5 | 15 | CRL1771 | 36 mg/kg | | | | Barnett | 1:20 | |
| 6 | 15 | D-PBS | N/A | | | | Barnett | 1:20 | |

In Vivo Animal Data

Mice were treated by intraperitoneal (IP; 0.5 ml) injection with 0.5 mg of monoclonal antibody 13-2, isotype control monoclonal antibody CRL-1771, or PBS. Eighteen hours after IgG administration, the mice were challenged with a single intravenous (IV) injection of *S. aureus* strain Barnett or *S. aureus* ATCC 25923. The mice were followed for 12 days at which point all remaining mice were sacrificed. Significant differences in the relative survival times between treatment groups were detected. Eighty-three percent (10/12) of the mice that received Mab 13-2, 13% (2/15) of the animals receiving CRL-1771, and 0% (0/15) that received PBS survived the bacterial challenge with *S. aureus* Barnett (13-2 vs. PBS, p<1.0001; 13-2 vs. CRL-1771, p=0.0009). Statistical analysis of the animal data was conducted using Kaplan-Meier Survival Analysis with a Mantel-Cox (logrank) test. In the experiment where *S. aureus* ATCC 25923 was the bacterial challenge, 67% (8/12) of the mice that were administered Mab 13-2 survived, 27% (4/12) survived in the CRL-1771 treated group, and only 7% (1/15) survived in the PBS group (13-2 vs. CRL-1771, p=0.02; 13-2 vs. PBS, 0.0002). These results clearly indicate that MSCRAMM specific monoclonal antibodies provide a significant level of protection against lethal infection with S. aureus strains.

Example 7

Isolation and Sequencing of Variable Region Sequences

A. Monoclonal Antibody 13-2.

Messenger RNA was isolated from ClfA 13-2 hybridoma cells using the Fast Track 2.0 kit (Invitrogen; cat #K4500). Briefly, $1.4 \times 10^8$ hybridoma cells cultured in DMEM-10 medium with 10% FBS were washed with PBS, pelleted by centrifugation then lysed in detergent containing Protein/RNase Degrader. PolyA$^+$ mRNA was isolated by affinity purification on oligo-dT cellulose. Synthesis of first strand cDNA was accomplished using 5 μg of mRNA and reverse transcriptase in a cDNA synthesis kit (Novagen; cat #69001-3) containing 20 pmol of 3' oligonucleotide mouse-specific primers (Novagen; cat # 69796 and 69812) for each variable heavy and variable light chain. A portion (5 to 50 ng) of the cDNA was amplified by the polymerase chain reaction (PCR) using the PCR Reagent System (Life Technologies; cat#10198-018) and a mouse variable heavy and light chain specific primer set (Novagen; cat# 70081-3, 5 pmol each) for 30 cycles (94 C hot start then cycles of 94 C for 1 min, 50 C for 1 min and 72 C for 1 min). PCR products were fractionated electrophoretically in a 1% ultra pure agarose gel in sodium acetate buffer and visualized by ethidium bromide staining. PCR fragments matching the predicted size were excised from the gel and purified using BIO 101 Geneclean spin columns (cat #1101-400) for ligation into the pCR2.1-TOPO (Invitrogen) plasmid, followed by transformation into competent TOP10 E. coli. (Invitrogen; cat# K4500). After isolating plasmid DNA using QIAprep Spin Miniprep Kit (QIAGEN; cat# 27106), positive clones with inserts were identified by restriction endonuclease digestion and agarose gel electrophoresis, followed by sequencing on an ABI automated sequencer using M13 Forward and M13 Reverse primers.

The resulting sequences were as follows:

13-2VLA-1 (Variable Light Sequence)

```
                                            DNA SEQ ID NO:5
AACATTATGATGACACAGTCGCCATCATCTCTGGCTGTGTCTGCAGGAGAA

AAGGTCACTATGAGCTGTAAGTCCAGTCAAAGTGTTTTATACAGTTCAAAT

CAGAAGAACTACTTGGCCTGGTACCAGCAGAAACCAGGGCAGTCTCCTAAA

CTACTGATCTACTGGGCATCCACTAGGGAATCTGGTGTCCCTGATCGCTTC

ACAGGCAGTGGATCTGGGACAGATTTTACTCTTACCATCAACAGTGTACAA

GCTGAAGACCTGGCAGTTTATTACTGTCATCAATACCTCTCCTCGCACACG

TTCGGAGGGGGGACCAAGCTGGAAATAAAA
                                            AMINO ACID SEQ ID NO:6
NIMMTQSPSSLAVSAGEKVTMSCKSSQSVLYSSNQKNYLAWYQQKPGQSPK

LLIYWASTRESGVPDRFTGSGSGTDFTLTINSVQAEDLAVYYCHQYLSSHT

FGGGTKLEIK
Amino acids representing a CDR are underlined
```

13-2VHC-3 (Variable Heavy Sequence)

```
                                            DNA SEQ ID NO:7
CAGGTGCATCTGAAGGAGTCAGGACCTGGCCTGGTGGCACCCTCACAGAGC

CTGTCCATCACATGCACTGTCTCTGGATTCTCATTATCCAGATATAATATA

CACTGGGTTCGCCAGCCTCCAGGAAAGGGTCTGGAGTGGCTGGGAATGATA

TGGGGTGGTGAAAACACAGACTATAATTCAGCTCTCAAATCCAGACTGAGC

ATCAGCAAGGACAACTCCAAGAGCCAAGTTTTCTTAAAAATGAACAGTCTG

CAAACTGATGACACAGCCATGTACTACTGTGCCAGCGCCTACTATGGTAAC

TCCTGGTTTGCTTACTGGGGCCAGGGGACTCTGGTCACTGTCTCTGCA
                                            AMINO ACID SEQ ID NO:8
QVHLKESGPGLVAPSQSLSITCTVSGFSLSRYNIHWVRQPPGKGLEWLGMI

WGGENTDYNSALKSRLSISKDNSKSQVFLKMNSLQTDDTAMYYCASAYYGN

SWFAYWGQGTLVTVSA
Amino acids representing a CDR are underlined
```

B. Monoclonal Antibody 12-9.

Messenger RNA was isolated from ClfA 12-9 hybridoma cells using the Fast Track 2.0 kit (Invitrogen; cat #K4500). Briefly, $1.4 \times 10^8$ hybridoma cells cultured in DMEM-10 medium with 10% FBS were washed with PBS, pelleted by centrifugation then lysed in detergent containing Protein/RNase Degrader. PolyA$^+$ mRNA was isolated by affinity purification on oligo-dT cellulose. Synthesis of first strand cDNA was accomplished using 5 μg of mRNA and reverse transcriptase in a cDNA synthesis kit (Novagen; cat #69001-3) containing 20 pmol of 3' oligonucleotide mouse-specific primers (Novagen; cat# 69796 and 69812) for each variable heavy and variable light chain. A portion (5 to 50 ng) of the cDNA was amplified by the polymerase chain reaction (PCR) using the PCR Reagent System (Life Technologies; cat#10198-018) and a mouse variable heavy and light chain specific primer set (Novagen; cat# 70081-3, 5 pmol each) for 30 cycles (94 C hot start then cycles of 94 C for 1 min, 50 C for 1 min and 72 C for 1 min). PCR products were fractionated electrophoretically in a 1% ultra pure agarose gel in sodium acetate buffer and visualized by ethidium bromide staining. PCR fragments matching the predicted size were excised from the gel and purified using BIO 101 Geneclean spin columns (cat #1101-400) for ligation into the pCR2.1-TOPO (Invitrogen) plasmid, followed by transformation into competent TOP10 E. coli. (Invitrogen; cat# K4500). After isolating plasmid DNA using QIAprep Spin Miniprep Kit (QIAGEN; cat# 27106), positive clones with inserts were identified by restriction endonuclease digestion and agarose gel electrophoresis, followed by sequencing on an ABI automated sequencer using M13 Forward and M13 Reverse primers.

The resulting sequences were as follows:

12-9VLA-1 (Variable Light Sequence)

```
                                            DNA SEQ ID NO:9
AACATTATGATGACACAGTCGCCATCATCTCTGGCTGTGTCTGCAGGAGAA

AAGGTCACTATGAGCTGTAAGTCCAGTCAAAGTGTTTTATACAGTTCAAAT

CAGAAGAACTACTTGGCCTGGTACCAGCAGAAACCAGGGCAGTCTCCTAAA

CTGCTGATCTACTGGGCATCCACTAGGGAATCTGGTGTCCCTGATCGCTTC
```

```
-continued
ACAGGCAGTGGATCTGGGACAGATTTTACTCTTACCATCAGCAGTGTACAA

GCTGAAGACCTGGCAGTTTATTACTGTCATCAATACCTCTCCTCGTACACG

TTCGGAGGGGGGACCAAGCTGGAAATAAAA

AMINO ACID SEQ ID NO:10
NIMMTQSPSSLAVSAGEKVTMSCKSSQSVLYSSNQKNYLAWYQQKPGQSPK

LLIYWASTRESGVPDRFTGSGSGTDFTLTISSVQAEDLAVYYCHQYLSSYT

FGGGTKLEIK
Amino acids representing a CDR are underlined
```

12-9VHC-1 (Variable Heavy Sequence)

```
                            DNA SEQ ID NO:11
CAGGTGCAGCTGAAGGAGTCAGGACCTGGCCTGGTGGCACCCTCACAGAGC

CTGTCCATCACATGCGCTATCTCTGGGTTCTCATTATCCAGATATAGTGTA

CACTGGGTTCGCCAGCCTCCAGGAAAGGGTCTGGAGTGGCTGGGAATGATA

TGGGGTGGTGGAAACACAGACTATAATTCAGCTCTCAAATCCAGACTGAGC

ATCAGCAAGGACAACTCCAAGAGCCAAGTTTTCTTAAAAATGAACAGTCTG

CAAACTGATGACACAGCCATGTATTACTGTGCCAGAAAAGGGGAATTCTAC

TATGGTTACGACGGGTTTGTTTACTGGGGCCAAGGGACTCTGGTCACTGTC

TCTGCA
                    AMINO ACID SEQ ID NO:12
QVQLKESGPGLVAPSQSLSITCAISGFSLSRYSVHWVRQPPGKGLEWLG

MIWGGGNTDYNSALKSRLSISKDNSKSQVFLKMNSLQTDDTAMYYCARKGE

FYYGYDGFVYWGQGTLVTVSA
Amino acids representing a CDR are underlined
```

C. Monoclonal Antibody 35-220.

Isolation and Sequencing of Variable Region Sequences:

Messenger RNA was isolated from ClfA 35-220 hybridoma cells using the Fast Track 2.0 kit (Invitrogen; cat #K4500). Briefly, 1.4×10⁸ hybridoma cells cultured in DMEM-10 medium with 10% FBS were washed with PBS, pelleted by centrifugation then lysed in detergent containing Protein/RNase Degrader. PolyA⁺ mRNA was isolated by affinity purification on oligo-dT cellulose. Synthesis of first strand cDNA was accomplished using 5 mg of mRNA and reverse transcriptase in a cDNA synthesis kit (Novagen; cat #69001-3) containing 20 pmol of 3' oligonucleotide mouse-specific primers (Novagen; cat# 69796 and 69812) for each variable heavy and variable light chain. A portion (5 to 50 ng) of the cDNA was amplified by the polymerase chain reaction (PCR) using the PCR Reagent System (Life Technologies; cat#10198-018) and a mouse variable heavy and light chain specific primer set (Novagen; cat# 70081-3, 5 pmol each) for 30 cycles (94 C hot start then cycles of 94 C for 1 min, 50 C for 1 min and 72 C for 1 min). PCR products were fractionated electrophoretically in a 1% ultra pure agarose gel in sodium acetate buffer and visualized by ethidium bromide staining. PCR fragments matching the predicted size were excised from the gel and purified using BIO 101 Geneclean spin columns (cat #1101-400) for ligation into the pCR2.1-TOPO (Invitrogen) plasmid, followed by transformation into competent TOP10 E. coli. (Invitrogen; cat# K4500). After isolating plasmid DNA using QIAprep Spin Miniprep Kit (QIAGEN; cat# 27106), positive clones with inserts were identified by restriction endonuclease digestion and agarose gel electrophoresis, followed by sequencing on an ABI automated sequencer using M13 Forward and M13 Reverse primers.

The resulting sequences were as follows:

35-220VLD-4 (Variable Light Sequence DNA SEQ ID NO:13)

```
AACATTATGATGACACAGTCGCCATCATCTCTGGCTGTGTCTGCAGGAGAA

AAGGTCACTATGAGCTGTAGGTCCAGTCAAAGTGTTTTATACAGTTCAAAT

CAGAAGAACTACTTGGCCTGGTACCAGCAGAAACCAGGGCAGTCTCCTACA

CTGCTGATCTACTGGGCATCCACTAGGGAATCTGGTGTCCCTGATCGCTTC

ACAGGCAGTGGATCTGGGACAGATTTTACTCTTACCATCAGCAGTGTACAA

GCTGAAGACCTGGCAGTTTATTACTGTCATCAATACCTCTCCTCGTACACG

TTCGGAGGGGGGACCAAGCTGGAAATAAAA
```

35-220VLD-4 (Variable Light Sequence AMINO ACID SEQ ID NO:14)

```
N I M M T Q S P S S L A V S A G E K V T M S C R S S

Q S V L Y S S N Q K N Y L A W Y Q Q K P G Q S P T L

L I Y W A S T R E S G V P D R F T G S G S G T D F T

L T I S S V Q A E D L A V Y Y C H Q Y L S S Y T F G

G G T K L E I K
Amino acids representing a CDR are underlined
```

35-220VHC-1 (Variable Heavy Sequence DNA SEQ ID NO:15)

```
CAGGTGCAGCTGAAGGAGTCAGGACCTGGCCTGGTGGCACCCTCACAGAGC

CTGTCCATCACATGCACTGTCTCTGGGTTCTCATTATCCAGATATAGTGTA

CACTGGGTTCGCCAGCCTCCAGGAAAGGGTCTGGAGTGGCTGGGAATGATA

TGGGGTGGTGGAAACACAGACTATAATTCAGCTCTCAAATCCAGACTGAGC

ATCACCAAGGACAACTCCAAGAGCCAAGTTTTCTTAAAAATGAACAGTCTG

CAAACTGATGACACAGCCATGTACTACTGTGCCACCGCCTACTATGGTAAC

TCCTGGTTTGCTTACTGGGGCCAAGGGACTCTGGTCACTGTCTCTGCA
```

35-220VHC-1 (Variable Heavy Sequence AMINO ACID SEQ ID NO:16)

```
Q V Q L K E S G P G L V A P S Q S L S I T C T V S G

F S L S R Y S V H W V R Q P P G K G L E W L G M I W

G G G N T D Y N S A L K S R L S I T K D N S K S Q V

F L K M N S L Q T D D T A M Y Y C A T A Y Y G N S W

F A Y W G Q G T L V T V S A
Amino acids representing a CDR are underlined
```

D. Monoclonal Antibody 35-006.

Isolation and Sequencing of Variable Region Sequences:

Messenger RNA was isolated from ClfA 35-006 hybridoma cells using the Fast Track 2.0 kit (Invitrogen; cat

K4500). Briefly, 1.4×10⁸ hybridoma cells cultured in DMEM-10 medium with 10% FBS were washed with PBS, pelleted by centrifugation then lysed in detergent containing Protein/RNase Degrader. PolyA⁺ mRNA was isolated by affinity purification on oligo-dT cellulose. Synthesis of first strand cDNA was accomplished using 5 mg of mRNA and reverse transcriptase in a cDNA synthesis kit (Novagen; cat #69001-3) containing 20 pmol of 3' oligonucleotide mouse-specific primers (Novagen; cat# 69796 and 69812) for each variable heavy and variable light chain. A portion (5 to 50 ng) of the cDNA was amplified by the polymerase chain reaction (PCR) using the PCR Reagent System (Life Technologies; cat#10198-018) and a mouse variable heavy and light chain specific primer set (Novagen; cat# 70081-3, 5 pmol each) for 30 cycles (94 C hot start then cycles of 94 C for 1 min, 50 C for 1 min and 72 C for 1 min). PCR products were fractionated electrophoretically in a 1% ultra pure agarose gel in sodium acetate buffer and visualized by ethidium bromide staining. PCR fragments matching the predicted size were excised from the gel and purified using BIO 101 Geneclean spin columns (cat #1101-400) for ligation into the pCR2.1-TOPO (Invitrogen) plasmid, followed by transformation into competent TOP10 *E. coli.* (Invitrogen; cat# K4500). After isolating plasmid DNA using QIAprep Spin Miniprep Kit (QIAGEN; cat# 27106), positive clones with inserts were identified by restriction endonuclease digestion and agarose gel electrophoresis, followed by sequencing on an ABI automated sequencer using M13 Forward and M13 Reverse primers.

The resulting sequences were as follows:

35-006VLD-1 (Variable Light Sequence DNA SEQ ID NO:21)

```
AACATTATGATGACACAGTCGCCATCATCTCTGGCTGTGTCTGCAGGAGAA
AAGGTCACTATGAGCTGTAAGTCCAGTCAAAGTGTTTTATACAGTTCAAAT
CAGAAGAACTACTTGGCCTGGTACCAGCAGAAACCAGGGCAGTCTCCTAAA
CTGCTGATCTACTGGGCATCCACTAGGGAATCTGGTGTCCCTGATCGCTTC
ACAGGCAGTGGATCTGGGACAGATTTTACTCTTACCATCAGCAGTGTACAA
GCTGAAGACCTGGCAGTTTATTGCTGTCATCAATACCTCTCCTCGTACACG
TTCGGAGGGGGGACCGAGCTGGAAATAAAA
```

35-006VLD-1 (Variable Light Sequence AMINO ACID SEQ ID NO:22)

```
N I M M T Q S P S S L A V S A G E K V T M S C K S S
Q S V L Y S S N Q K N Y L A W Y Q Q K P G Q S P K L
L I Y W A S T R E S G V P D R F T G S G S G T D F T
L T I S S V Q A E D L A V Y C C H Q Y L S S Y T F G
G G T E L E I K
Amino acids representing a CDR are underlined
```

35-006VHC-1 (Variable Heavy Sequence DNA SEQ ID NO:23)

```
CAGGTGCAGCTGAAGGAGTCAGGACCTGGCCTGGTGGCACCCTCACAGAGC
CTGTCCATCACATGCACTGTCTCTGGGTTCTCATTATCCAGATATAGTGTA
CACTGGGTTCGCCAGCCTCCAGGAAAGGGTCTGGAGTGGCTGGGAATGATA
TGGGGTGGTGGAAGCACAGACTATAATTCAGCTCTCAAATCCAGACTGAAC
ATCAGCAAGGACAACTCCAAGAGCCAAGTTTTCTTAAAAATGAACAGTCTG
CAAACTGATGACACAGCCATGTACTACTGTGCCAGAAGGCTCTGGTACTTC
GATGTCTGGGGCGCAGGGACCACGGTCACCGTCTCCTCA
```

35-006VHC-1 (Variable Heavy Sequence AMINO ACID SEQ ID NO:24)

```
Q V Q L K E S G P G L V A P S Q S L S I T C T V S G
F S L S R Y S V H W V R Q P P G K G L E W L G M I W
G G G S T D Y N S A L K S R L N I S K D N S K S Q V
F L K M N S L Q T D D T A M Y Y C A R R L W Y F D V
W G A G T T V T V S S
Amino acids representing a CDR are underlined
```

Example 8

Generation of Chimeric 12-9 with Equivalence in Binding Kinetics and Whole Cell Reactivity to Murine 12-9

Chimeric 12-9 was generated using human constant regions (light chain: kappa; heavy chain: G1, 3 or 4) isolated from whole blood of human volunteers (selection of Poly A RNA and PCR amplification of first strand cDNA). For expression in mammalian cells, a unique restriction site Bsm 1 was added to the 5' end of both the heavy and light chain variable region sequences. At the 3' end (the splice junction to the respective constant region) a Bsiw1 site was added to the light chain variable region and an Apa1 site was added to the heavy chain variable region. This was accomplished through the design of oligonucleotide primers and PCR amplification of the appropriate 12-9 DNA template followed by confirmatory DNA sequencing.

Expression of chimeric versions of 12-9 protein was accomplished using the pCEP4 (Invitrogen, cat# V044-50) mammalian expression vector containing a human immunoglobulin leader secretion sequence (Bsm1 as the cloning site) with a kappa constant region for light chain expression or gamma (1, 3 or 4) constant region for heavy chain expression. The mammalian expression plasmid was designed for expression of both heavy and light chains with separate hCMV promoters on the same plasmid or the expression of the light and heavy chains on separate pCEP4 plasmids via co-transfection. Functional chimeric 12-9 was expressed after transfection of plasmid DNA containing the heavy and light chains of 12-9 into HEK293 EBNA cells with Fugene (Roche Diagnostic, cat# 1814443) under hygromycin selection (300 μg/ml). Supernatants were harvested and analyzed by Biacore for binding kinetics and flow cytometry for binding to *S. aureus* cells.

Figure 2:
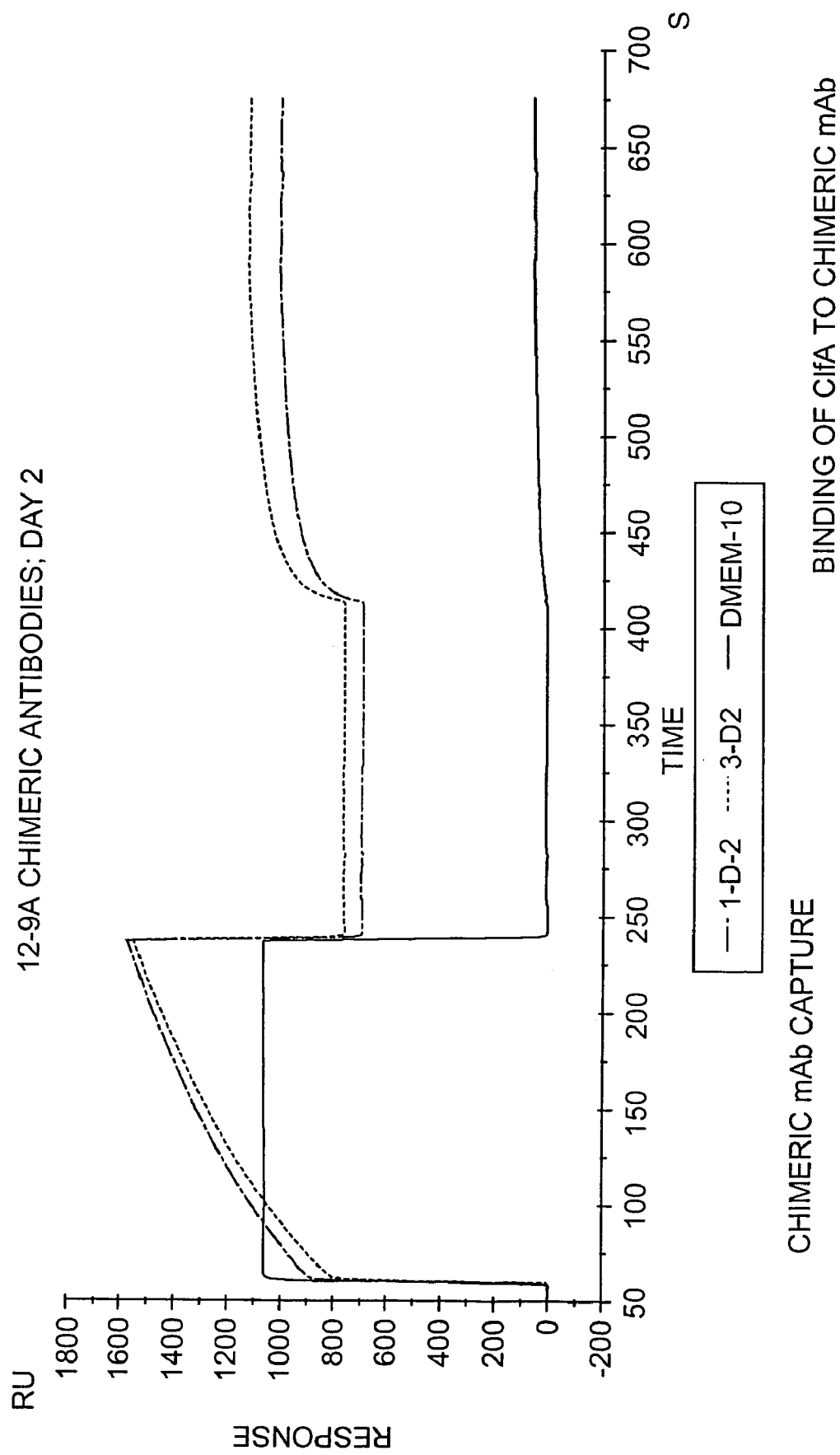
FIG. 2 is a graph of a biacore analysis of the Chimeric monoclonal antibody 12-9 in accordance with the present invention.
Figure 3:
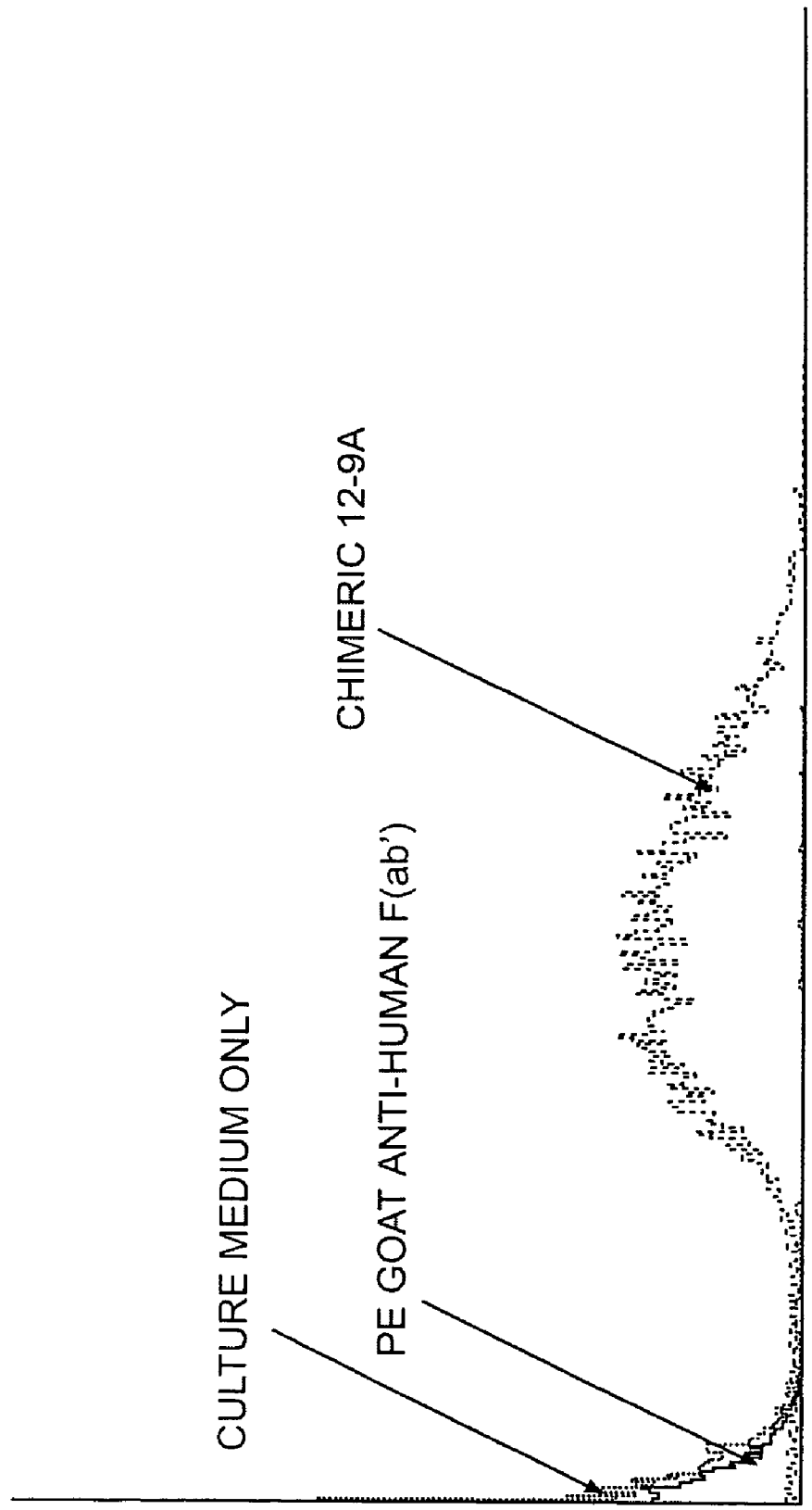
FIG. 3 is a graph of a flow cytometric analysis of monoclonal antibody Chimeric 12-9 showing binding to *S. aureus* (Strain Newman).
Figure 4:
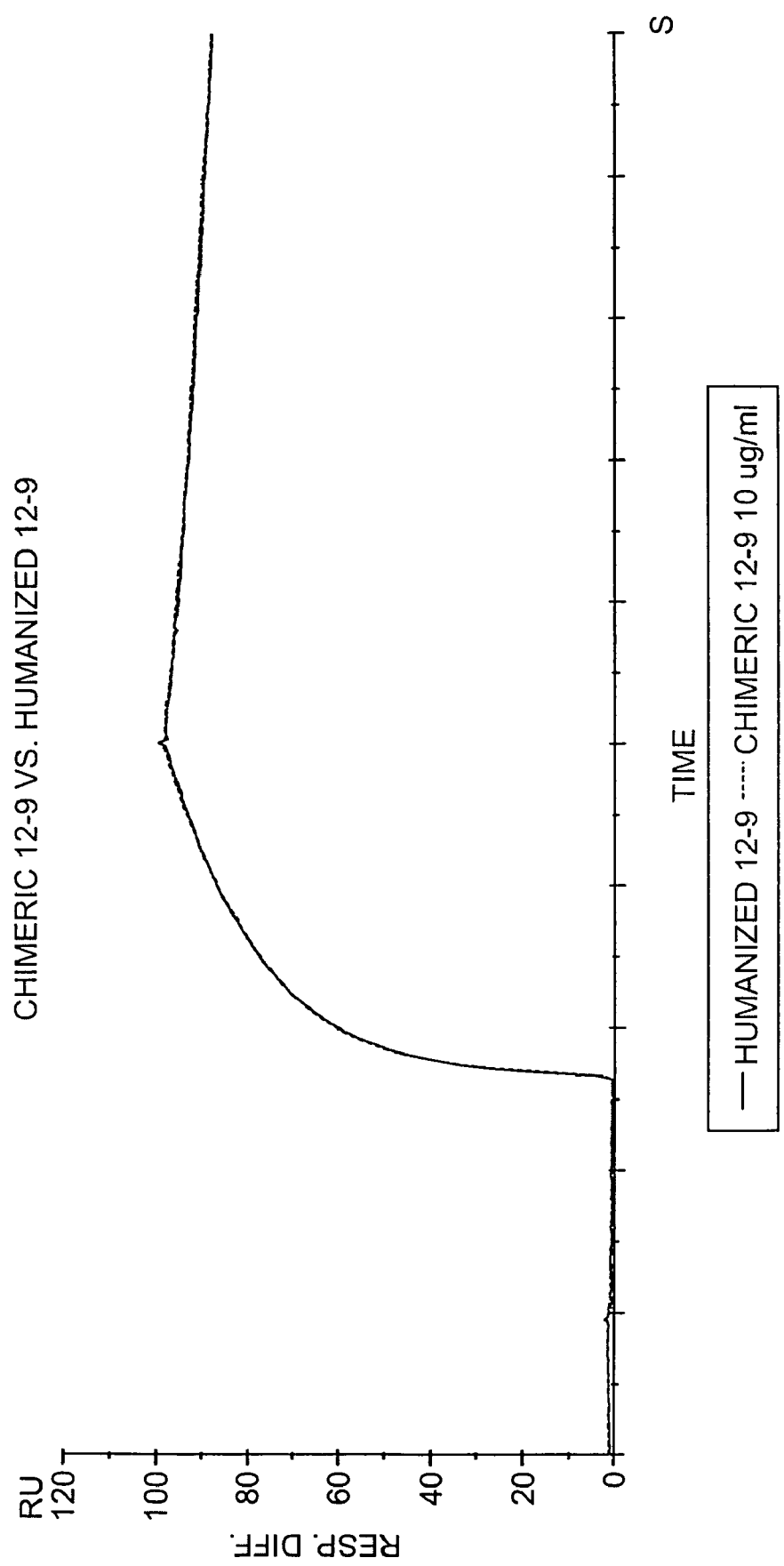
FIG. 4 is a graph showing binding affinity to ClfA of Chimeric and Humanized monoclonal antibody 12-9 in accordance with the invention.
Figure 5:
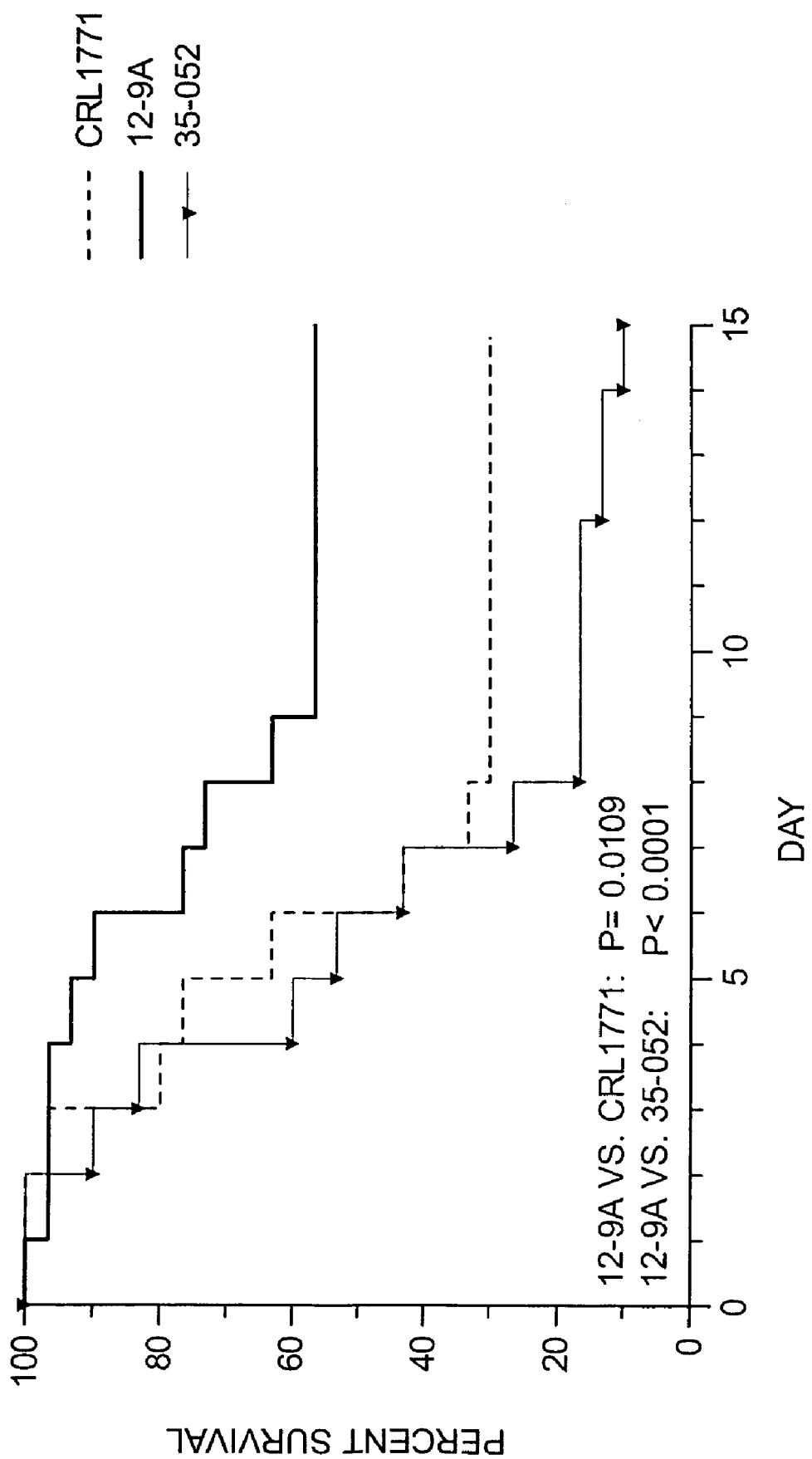
FIG. 5 is a graph showing the protection against *Staphylococcus aureus* murine lethal challenge model.
Figure 6:
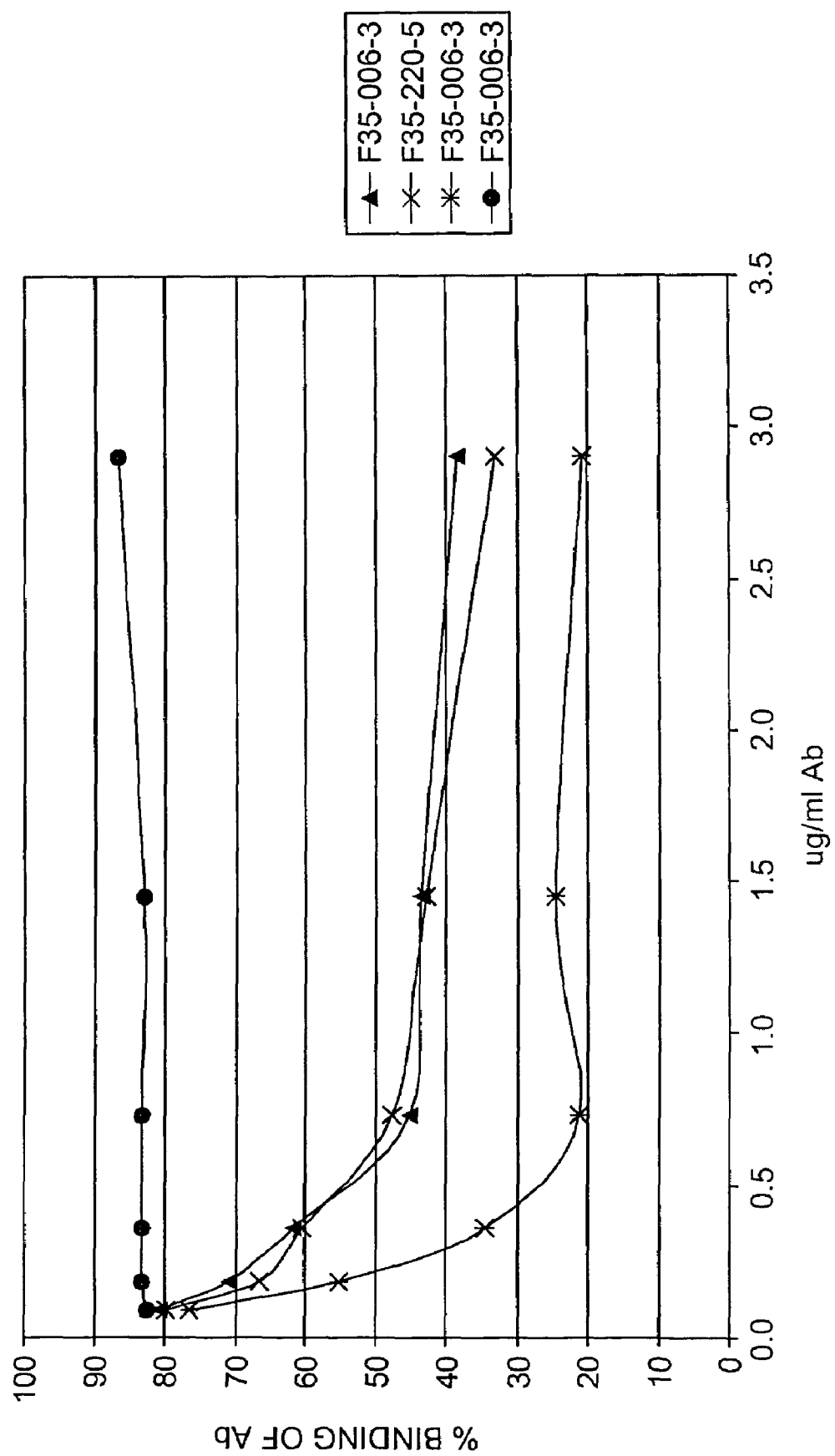
FIG. 6 is a graph showing the whole cell inhibition of *S. aureus* adherence to immobilized fibrinogen using the monoclonal antibodies of the present invention.

The results represented in FIGS. 2 and 3 with recombinant chimeric 12-9 confirm that the sequence of the heavy and light chains of 12-9 replicates the binding kinetics and specificity of the original 12-9 characterized as a hybridoma supernatant.

Example 9

Humanization of the Heavy and Light Chain Variable Regions of 12-9

This process of humanization focuses on changing only the solvent exposed residues of the mouse variable regions that are not involved in the molecule's specificity and affinity for the ClfA target antigen. The information for these determinations utilized solvent availability determinations published by Padlan (A possible procedure for reducing the immunogenicity of antibody variable domains while preserving their ligand binding properties. Molecular Immunology, 28(4); 489-498, 1991), and molecular modeling in silico or algorithms to determine T-cell epitopes were not used to make these determinations.

The approach represents a process by which the mouse variable region residues of the light and heavy chain are changed by site directed mutagenesis to reflect the surface exposed architecture of the most homologous human variable region from the public database. Specifically, the amino acids defining the variable heavy and light chains were assigned a Kabot position number and "exposure" designation based on Padlan, allowing the alignment of the amino acids from each human framework sub-group (I-III for the heavy chain and I-IV for the light chain). To support this analysis, a BLAST search was carried out on the human immunoglobulin database as well as the entire protein database where the variable region with the highest homology to the mouse sequence (both germ-line and mature) were chosen and aliened with the murine sequence of interest. Once aliened, the human subgroup with the highest homology to the mouse sequence was identified. The exposed mouse amino acid residues were mutated to mimic the most homologous human subgroup. In cases were there was more than one amino acid found in the subgroup at that position, the amino acid represented in the human germ line sequence with the highest homology to the 12-9 was used. These changes were accomplished with mutagenic oligonucleotides via PCR followed by conformational DNA sequencing.

12-9VL-Hu (Humanized Variable Light Sequence DNA SEQ ID NO:17, Humanized 12-9)

```
GACATTGTGATGACACAGTCGCCAGACTCTCTGGCTGTGTCTCTGGGAGAA
AGGGTCACTATGAACTGTAAGTCCAGTCAAAGTGTTTTATACAGTTCAAAT
CAGAAGAACTACTTGGCCTGGTACCAGCAGAAACCAGGGCAGTCTCCTAAA
CTGCTGATCTACTGGGCATCCACTAGGGAATCTGGTGTCCCTGATCGCTTC
AGCGGCAGTGGATCTGGGACAGATTTTACTCTTACCATCAGCAGTGTACAA
GCTGAAGACCTGGCAGTTTATTACTGTCATCAATACCTCTCCTCGTACACG
TTCGGAGGGGGGACCAAGCTGGAAATAAAA
```

12-9VL-Hu (Humanized Variable Light Sequence AMINO ACID SEQ ID NO:18, Humanized 12-9)

```
DIVMTQSPDSLAVSLGERVTMNCKSSQSVLYSSNQKNYLAWYQQKPGQSPK
LLIYWASTRESGVPDRFSGSGSGTDFTLTISSVQAEDLAVYYCHQYLSSYT
FGGGTKLEIK
Amino acids representing a CDR are underlined,
amino acids in bold represent humanization changes
```

12-9VH-Hu (Humanized Variable Heavy Sequence DNA SEQ ID NO:19, Humanized 12-9)

```
CAGGTGCAGCTGAAGGAGTCAGGACCTGGCCTGGTGAAGCCCTCACAGACC
CTGTCCATCACATGCACCATCTCTGGGTTCTCATTATCCAGATATAGTGTA
CACTGGGTTCGCCAGCCTCCAGGAAAGGGTCTGGAGTGGCTGGGAATGATA
TGGGGTGGTGGAAACACAGACTATAATTCAGCTCTCAAATCCAGACTGAGC
ATCAGCAAAGACAACTCCAAGAACCAAGTTTTCTTAAAAATGAACAGTCTG
ACCGCCGCTGACACAGCCGTGTATTACTGTGCCAGAAAAGGGGAATTCTAC
TATGGTTACGACGGGTTTGTTTACTGGGGCCAAGGGACTCTGGTCACTGTC
TCTTCC
```

12-9VH-Hu (Humanized Variable Heavy Sequence AMINO ACID SEQ ID NO:20, Humanized 12-9)

```
QVQLKESGPGLVKPSQTLSITCTISGFSLSRYSVHWVRQPPGKGLEWLGMI
WGGGNTDYNSALKSRLSISKDNSKNQVFLKMNSLTAADTAVYYCARKGEFY
YGYDGFVYWGQGTLVTVSS
Amino acids representing a CDR are underlined,
amino acids in bold represent humanization changes
```

Example 10

Comparison of the ClfA Monoclonal Antibodies, 12-9A (INH-M010001) and 35-052.1 (INH-M01016), with the Isotype Matched Control CRL1771 Antibody, INH-M000029, in a Mouse Sepsis Model Using Methicillin Resistant S. aureus Strain 67-0 (MRSA)

The purpose of this example is to characterize the protective effects of the ClfA monoclonal antibodies, 12-9A (INH-M010001) and 35-052.1 (INH-M01016) compared with the isotype-matched control CRL1771 antibody (INH-M000029) using a 0.3 mg dose of antibody and S. aureus strain 67-0 in a mouse sepsis model.

| Species | Strain | Sex | Number | Age* | Weight* | Source |
|---|---|---|---|---|---|---|
| Mice | Balb/C | Female | 90 | 4-5 weeks | 12-16 grams | Taconic Farms, Inc. (Germantown, NY) |

*Estimated range at initiation of study.

Dosing was performed by the administration of an intraperitoneal (i.p.) injection of monoclonal antibody to the appropriate animals (see below). Administration of the antibody was performed approximately 18 hours prior to the intravenous (i.v.) injection of S. aureus. Systemic infection was measured using a single parameter (mortality).

| Group # | No. of Mice | TREATMENT | | | | | CHALLENGE | | |
|---|---|---|---|---|---|---|---|---|---|
| | | Antibody | Dose | Route | Frequency | Time Point* | Bacteria | CFU | Volume/ Route |
| 1 | 30 | 12-9A | 0.3 mg. | i.p. | Once | −18 hr. | S. aureus 67-0 | ~$10^8$ | 0.1 ml./i.v. |
| 2 | 30 | 35-052 | 0.3 mg. | | | | | | |
| 3 | 30 | CRL1771 | 0.3 mg. | | | | | | |

*Time points reflect hours post bacterial challenge.

Preparation, Storage and Handling:

Staphylococcus aureus

MRSA strain 67-0 cells were taken from a frozen glycerol stock and were inoculated onto a single blood agar plate and grown for 24 hours at 37° C. Single colonies were then transferred to new blood agar plates. Eighty plates were inoculated to prepare 50 mls of final frozen stock. The plates were then incubated for 24 hours at 37° C. Following incubation, the colonies were scraped off the surface of each plate into four 50 ml tubes containing 10 mls of 1×PBS (20 plates per tube) while gently vortexing to remove the bacteria from the scraper. An additional 10 mls of 1×PBS was then added to the 10 mls of bacterial suspension, while vigorously vortexing to facilitate separation of any agar debris from the bacteria. The suspension was pelleted by centrifugation, 3500×g at 4° C. for 10 minutes. The bacteria was washed in D-PBS and resuspended in 50 mls of freezing media. The bacterial stock was placed into 1 ml aliquots by snap freezing in an ethanol/dry ice bath and placed in an −80° C. freezer. The concentration (CFU/ml) of the frozen stock was determined by thawing 1 ml aliquot of stock, and preparing serial dilutions from $10^{-5}$ to $10^{-11}$. Dilutions were plated in duplicate on blood agar plates and incubated for 37° C. for 16-18 hours. The CFU/ml was determined (CFU/ml=(average # colonies×dilution factor)/0.050 mls) and averaged for each dilution to determine the average CFU/ml. On the day of injection, aliquots of each strain will be thawed, combined into one tube and vortexed. Dilutions of each stock will then be prepared.

ClfA 12-9A Monoclonal Antibody, INH-M010001 (LN: IAA2E1354)

The 12-9A monoclonal antibody (IgG$_1$ subtype) was purified from serum free hybridoma culture medium using protein G affinity chromatography. The material was reported to be at a concentration of 7.0 mg/ml with an endotoxin concentration of 1.0 EU/mg of protein. The material was stored refrigerated at 4° C. On the day of injection, the material will be diluted to 0.6 mg/ml and 0.5 ml will be administered via an intraperitoneal injection to the appropriate group of animals. The final dose that will be administered will be 0.3 mg of IgG.

ClfA 35-052.1 Monoclonal Antibody, INH-M01016 (LN: IAA2H1422)

The 35-052 monoclonal antibody (IgG$_1$ subtype) was purified from serum free hybridoma culture medium using protein G affinity chromatography. The material was reported to be at a concentration of 4.2 mg/ml with an endotoxin concentration of 1.0 EU/mg of protein. The material was stored refrigerated at 4° C. On the day of injection, the material will be diluted to 0.6 mg/ml and 0.5 ml will be administered via an intraperitoneal injection to the appropriate group of animals. The final dose that will be administered will be 0.3 mg of IgG.

Control CRL 1771 Monoclonal Antibody (INH-M000029, LN: IAA2E1337)

The CRL 1771 monoclonal antibody (IgG$_1$ subtype) was purified from serum free hybridoma culture medium using protein G affinity chromatography. The material was reported to be at a concentration of 5.0 mg/ml with an endotoxin concentration of 0.2 EU/mg of protein. The material was stored refrigerated at 4° C. On the day of injection, the material will be diluted 0.6 mg/ml and 0.5 ml will be administered via an intraperitoneal injection. The final dose that will be administered will be 0.3 mg of IgG.

Housing, Food, Water and Environment:

Upon receipt, all animals were examined and group housed (5/cage) in polycarbonate shoebox style cages with absorbent bed-o-cobb bedding. All animals have free access to feed (Harlan/Teklad Mouse Pelleted Diet #7012) and tap water with a 12-hour light-dark cycle. All aspects of the animal care and the required husbandry conditions will be in accordance with the NIH *Guide for the Care and Use of Laboratory Animals*.

Identification and Randomization:

All mice were uniquely identified by tail tattoo before treatment. Prior to treatment, the mice were individually weighed and their health re-evaluated.

Mice were assigned to treatment groups based on randomization by stratified body weights.

The data demonstrate the therapeutic value of an anti-ClfA antibody such as 12-9 that interferes with ClfA—fibrinogen adhesion compared with a non ClfA specific isotype control (CRL 1771) as well as a specific control (35-052) that recognizes ClfA at a site independent of ClfA-fibrinogen binding.

Example 11

*S. aureus* Strain Recognition of 12-9 and 35-052 Compared to Isotype Control (CRL 1771)

*S. aureus* bacterial samples (strains Newman-WT, 67-0, 560 Sal 1, 203 Sal 2, 451 Sal 4, 206 Sal5, 397 Sal 6, 49, 189, 203 and 4046) were collected at 3 hr and overnight, washed and incubated with Mab 12-9, 35-52 or 1771 alone (control) at a concentration of 2 mg/ml after blocking protein A sites with rabbit IgG (50 mg/ml). The *S. aureus* strains containing a Sal designation represent 5 distinct lineages accounting for 65.68% of all clinical isolates (Booth, et al., *Infect. Immun.* 69, 345-353, 2001). As well, Newman ClfA::emr (ClfA knockout) and NewmanSpa::kan (Protein A knockout) were analyzed in the same manner as specificity controls. Following incubation with antibody, bacterial cells were incubated with Goat-F$_{(ab')2}$-Anti-Mouse-F$_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured.

TABLE VI

S. aureus Strain Reactivity

| S. aureus Strain | Culture Time | Fluorescence Intensity (Geometric Mean) | | |
|---|---|---|---|---|
| | | 12-9 | 35-052 | CRL 1771 |
| Newman WT | 3 hr | 30.8 | 11.1 | 0.5 |
| | overnight | 44.3 | 30 | 0.9 |
| 67-0 | 3 hr | 11.2 | 4.2 | 2 |
| | overnight | 27.6 | 1.9 | 1.1 |
| 560 SAL 1 | 3 hr | 28.8 | 8.4 | 3.9 |
| | overnight | 36.1 | 6.2 | 1.2 |
| 203 SAL2 | 3 hr | 16.1 | 0.6 | 2.2 |
| | overnight | 40.4 | 1.9 | 1.4 |
| 451 SAL4 | 3 hr | 1.1 | 0 | 0 |
| | overnight | 12.9 | 0 | 0 |
| 206 SAL5 | 3 hr | 8.8 | 1.3 | 1 |
| | overnight | 33.5 | 7.7 | 0.9 |
| 397 SAL6 | 3 hr | 28.9 | 7.9 | 0.3 |
| | overnight | 62.1 | 40.0 | 1.0 |
| 49 Europe | 3 hr | 7.3 | 1.2 | 0 |
| 189 Japan | overnight | 11.3 | 5.7 | 0 |
| | 3 hr | 11.0 | 0 | 0 |
| 203 Singapore | overnight | 15.7 | 0 | 0 |
| | 3 hr | 22.1 | 3.3 | 0.1 |
| 4046 USA | overnight | 15.4 | 2.5 | 0.2 |
| | 3 hr | 27.7 | 2.5 | 1.3 |
| | overnight | 23.5 | 1.2 | 0.3 |
| Newman ClfA::emr | 3 hr | 0.2 | 0.3 | 0.2 |
| | overnight | 1.4 | 0.8 | 0.9 |
| Newman Spa::kan | 3 hr | 18.6 | 4.9 | 0 |
| | Overnight | 23.9 | 9.2 | 0 |

▨ Indicates positive activity

This data highlights the importance of selecting an anti-ClfA antibody (such as 12-9) that is capable of recognizing a functional epitope on the ClfA molecule: i.e. the binding site for fibrinogen.

Another set of S. aureus isolates, a representation of 11 different clonal genotype complexes identified as disproportionately common as causes of disease, derived via multi-locus sequence typing (Day, et. al. 2001. A link between virulence and ecological abundance in natural populations of Staphylococcus aureus. Science, 292:114-116). Each strain was tested for reactivity against 12-9 by flow cytometry as described above.

TABLE VII 12-9 Reactivity with S. aureus isolates.

| S. aureus Strain Designation | Sequence Type | Clonal Complex | 12-9 Reactivity |
|---|---|---|---|
| 16 | 25 | 8 | + |
| 96 | 47 | 10 | + |
| 117 | 12 | 4 | + |
| 138 | 30 | 9 | + |
| 150 | 9 | 14 | + |
| 160 | 34 | 7 | + |
| 207 | 15 | 5 | + |
| 252 | 36 | 9 | + |
| 315 | 8 | 3 | + |
| 364 | 39 | 9 | + |
| 396 | 30 | 9 | + |
| 433 | 5 | 2 | + |
| 434 | 8 | 3 | + |
| 451 | 5 | 2 | + |
| 456 | 45 | 10 | + |
| 458 | 15 | 5 | + |
| 476 | 1 | 1 | + |
| 481 | 47 | 10 | + |
| 512 | 1 | 1 | + |
| 597 | 25 | 8 | + |
| 720 | 22 | 7 | + |
| 730 | 45 | 10 | + |
| 837 | 12 | 4 | + |
| 863 | 20 | 11 | + |
| 888 | 39 | 9 | + |
| 959 | 34 | 9 | + |

This reactivity further demonstrates the conservation of the 12-9 epitope on ClfA across isolated strains of S. aureus, suggesting that ClfA-fibrinogen binding is functionally conserved.

Example 12

Variable Region Homology in Anti-ClfA Antibodies That Inhibit Whole Cell S. aureus Binding An unexpected result from the selection of anti-ClfA antibodies based on there ability to inhibit ClfA binding to fibrinogen was the similarity in the complementary determining region (CDR) amino acid sequences of the light and heavy variable chain regions. To profile this, anti-ClfA antibodies were selected on the basis of whole cell S. aureus inhibition of binding to fibrinogen-coated plates using the following procedure: Antibodies of interest were diluted serially starting at 4 µg/ml in assay buffer. Concurrently, an overnight culture of S. aureus (Newman spa::kan) was washed, blocked with rabbit IgG then stained with Syto 13 cell permeable fluorescent DNA stain and incubated for 10 min. Equal volumes of stained cells and diluted antibody were mixed and incubated at 4° C. for 30 min then each sample added to duplicate wells of a human fibrinogen coated/blocked microtiter plate. Plates were incubated at 4° C. for one hour, washed, buffer added to each well and read in a fluorescent plate reader.

The variable light and heavy chains of the anti-ClfA monoclonals, 12-9, 13-2, 35-006 and 35-220 as well as CRL 1771 (non-specific control) were cloned and sequenced to derive a predicted amino acid sequence in the following manner: Briefly, $1.4 \times 10^8$ hybridoma cells cultured in DMEM-10 medium with 10% FBS were washed with PBS, pelleted by centrifugation then lysed in detergent containing Protein/RNase Degrader. PolyA$^+$ mRNA was isolated by affinity purification on oligo-dT cellulose. Synthesis of first strand cDNA was accomplished using 5 mg of mRNA and reverse transcriptase in a cDNA synthesis kit (Novagen; cat #69001-3) containing 20 pmol of 3' oligonucleotide mouse-specific primers (Novagen; cat# 69796 and 69812) for each variable heavy and variable light chain. A portion (5 to 50 ng) of the cDNA was amplified by the polymerase chain reaction (PCR) using the PCR Reagent System (Life Technologies; cat#10198-018) and a mouse variable heavy and light chain specific primer set (Novagen; cat# 70081-3, 5 pmol each) for 30 cycles (94 C hot start then cycles of 94 C for 1 min, 50 C for 1 min and 72 C for 1 min). PCR products were fractionated electrophoretically in a 1% ultra pure agarose gel in sodium acetate buffer and visualized by ethidium bromide staining. PCR fragments matching the predicted size were excised from the gel and purified using BIO 101 Geneclean spin columns (cat #1101-400) for ligation into the pCR2.1-TOPO (Invitrogen) plasmid, followed by transformation into competent TOP10 E. coli. (Invitrogen; cat# K4500). After isolating plasmid DNA using QIAprep Spin Miniprep Kit (QIAGEN; cat# 27106), positive clones with inserts were identified by restriction endonuclease digestion and agarose gel electrophoresis, followed by sequencing on an ABI automated sequencer using M13 Forward and M13 Reverse primers.

As shown in FIG. 7, the data shows that there is considerable conservation in the most variable portion of the immunoglobulin chains that define the binding specificity for anti-ClfA monoclonals with inhibition of *S. aureus* binding to fibrinogen. This homology is represented from three different hybridoma-generating fusions (12,13 and 35); under variable conditions such as the make-up of the Clf-A antigen, the method and sequence of the immunizations prior to fusion. In particular, this data revealed consensus conserved regions in the CDR1 and CDR2 regions of the variable heavy chain of monoclonal antibodies binding to ClfA as well as conserved regions in the CDR1, CDR2, and CDR3 regions of the variable light chains of the antibodies of the present invention. This data thus shows that preparation of antibodies with the conserved sequences should have the same binding properties and thus will fall within the scope of the present invention.

Accordingly, in accordance with the present invention, antibodies which will bind to ClfA can be prepared using variable light or heavy chains which have the same key CDR regions as indicated in the consensus of FIG. 8. In particular, these antibodies will include those which have a variable heavy chain wherein the CDR1 region includes the sequence SEQ ID NO:25 RYSVH, and/or a CDR2 region that includes the sequence SEQ ID NO:26 MIWGGGNTDYNSALKS, and a variable light chain that has a CDR1 region that includes the sequence SEQ ID NO:27 KSSQSVLYSSNQKNYLA, a CDR2 region that includes the sequence SEQ ID NO:28 WASTRES, and/or a CDR3 region that includes the sequence SEQ ID NO:29 HQYLSSYT.

Example 13

Expression of Humanized 12-9 For Pre-clinical and Clinical Use

For simultaneous expression of the heavy and light immunoglobulin polypeptide chains, the two genes were cloned into a single plasmid with each gene under the control of a separate hCMV-MIE promoter. This double gene vector holds a single copy of the GS selectable marker (Lonza; Slough, UK) for introduction into the host cell in a single transfection event. Cells were transfected using Fugene-6 (Roche) under conditions suggested by the manufacturer. Supernatants were tested from transient or stably derived cell lines and compared with murine and chimeric derived 12-9.

This example demonstrates that humanized 12-9 can be humanized, cloned and expressed a single expression cassette capable of yields to support commercial scale quality and purity.

What is claimed is:

1. A method of treating an infection of *S. aureus* comprising administering an antibody or binding fragment thereof comprising a variable light chain having the amino acid sequence SEQ ID NO:6 and a variable heavy chain having the amino acid sequence SEQ ID NO:8, or a variable light chain having the amino acid sequence SEQ ID NO:10 and a variable heavy chain having the amino acid sequence SEQ ID NO:12, or a variable light chain having the amino acid sequence SEQ ID NO:18 and a variable heavy chain having the amino acid sequence SEQ ID NO:20.

* * * * *